United States Patent [19]
Silkoff et al.

[11] Patent Number: 6,010,459
[45] Date of Patent: *Jan. 4, 2000

[54] METHOD AND APPARATUS FOR THE MEASUREMENT OF COMPONENTS OF EXHALED BREATH IN HUMANS

[76] Inventors: Philip E. Silkoff, 640 Roselawn Avenue, Appartment 610, Toronto, Ontario M5N 1K9; Patricia A. McClean, 55 Queen'Drive, Weston, Ontario, M9N 2H3, both of Canada

[*] Notice: This patent is subject to a terminal disclaimer.

[21] Appl. No.: 08/827,703

[22] Filed: Apr. 9, 1997

Related U.S. Application Data

[63] Continuation-in-part of application No. 08/629,594, Apr. 9, 1996, Pat. No. 5,795,787
[60] Provisional application No. 60/017,251, May 10, 1996.

[51] Int. Cl.[7] ........................................................ A61B 5/08
[52] U.S. Cl. ...................... 600/532; 600/529; 128/200.26
[58] Field of Search .................... 600/529, 532; 128/200.26, 204.22, 204.23, 200.15

[56] References Cited

U.S. PATENT DOCUMENTS

| | | |
|---|---|---|
| 3,726,270 | 4/1973 | Griffis et al. . |
| 3,785,370 | 1/1974 | Richards et al. . |
| 3,951,607 | 4/1976 | Fraser . |
| 4,083,367 | 4/1978 | Portner et al. . |
| 4,090,078 | 5/1978 | Heim . |
| 4,090,518 | 5/1978 | Elam ................................. 128/207.15 |
| 4,202,352 | 5/1980 | Osborn . |
| 4,688,568 | 8/1987 | Frass et al. ........................ 128/207.15 |
| 4,735,777 | 4/1988 | Mitsui et al. . |
| 4,772,559 | 9/1988 | Preti et al. . |
| 4,796,639 | 1/1989 | Snow et al. . |
| 4,872,483 | 10/1989 | Shah ...................................... 137/557 |
| 5,042,501 | 8/1991 | Kenney et al. . |
| 5,081,871 | 1/1992 | Glaser . |
| 5,443,063 | 8/1995 | Greenberg ........................... 128/207.15 |
| 5,447,165 | 9/1995 | Gustafsson . |
| 5,474,060 | 12/1995 | Evans ................................. 128/204.22 |
| 5,531,218 | 7/1996 | Krebs . |
| 5,651,358 | 7/1997 | Briend et al. ....................... 128/203.12 |
| 5,653,229 | 8/1997 | Greenberg ........................... 128/207.15 |
| 5,795,787 | 8/1998 | Silkoff et al. ........................... 436/116 |

FOREIGN PATENT DOCUMENTS

| | | |
|---|---|---|
| 0 573 060 A3 | 12/1993 | European Pat. Off. . |
| 0 650 051 A2 | 4/1995 | European Pat. Off. . |
| 3844455 | 8/1989 | Germany . |
| 2171017 | 8/1986 | United Kingdom .............. 128/207.15 |
| 95/02181 | 1/1995 | WIPO . |

OTHER PUBLICATIONS

Brooks, Lee J. et al., "Reproducibility and accuracy of airway area by acoustic reflection;" J. Appl. Physiol.: Respirat. Environ. Exercise Physiol. 57(3): 777–787, 1984.

Fredberg, Jeffrey et al. "Acoustic Determinants of Respiratory System Properties" A special issue of Annals of Biomedical Engineering, Pergamon Press, New York (Gerald M. Saidel et al., eds) 9: 463–473 (1981).

Fredberg, Jeffrey J. et al., "Airway area by acoustic reflections measured at the mouth;" J. Appl. Physiol.: Respirat. Environ. Exercise Physiol. 48(5):749–758, 1980.

(List continued on next page.)

*Primary Examiner*—John G. Weiss
*Assistant Examiner*—Joseph F. Weiss, Jr.
*Attorney, Agent, or Firm*—Morgan, Lewis & Bockius LLP

[57] ABSTRACT

Methods and related equipment for measuring components of exhaled breath of a subject are provided which involve causing the subject to exhale into an appropriate apparatus for receiving exhaled breath; increasing the pressure in the mouth of the subject to a level sufficient to close the vellum and isolate the nasopharynx during exhalation; a means of monitoring nasal $CO_2$ to conrirm vellum closure; and measuring the level of one or more components of the collected exhaled breath. Endogenous nitric oxide is a preferred component of exhaled breath for monitoring and analysis.

23 Claims, 9 Drawing Sheets

OTHER PUBLICATIONS

Kimberly, Brent et al. "Nasal Contribution to Exhaled Nitric Oxide at Rest and during Breathholding in Humans" The American Journal of Respiratory and Critical Care Medi 153:829–836, 1996.

Massaro, AF et al. "Expired nitric oxide levels during treatment of acute asthma" Am. J. Respi., Critical Care Med. vol. 152, No. 2, Aug. 1995, 800–803.

Paredi, P. et al., "Factors Influencing Exhaled Nitric Oxide Levels During Reservoir Collection for Subsequent or Delayed Analysis", American Journal of Respiratory and Critical Care Medicine vol. 157:A614, Mar. 1998.

Robbins, RA et al. "Measurement of exhaled nitric oxide by three different techniques", Am. J. Respir. Crit. Care Med., vol. 153, No. 5, May 1996, 1631–1635.

Rubinstein, I. et al., "Effect of mouthpiece, noseclips, and head position on airway area measured by acoustic reflections;" J. Appl. Physiol. 63(4): 1469–1474, 1987.

Sidell, R. et al., Noninvasive Inference of Airway Network Geometry From Broadband Lung Reflection Data; Journal of Biomechanical Engineering, vol. 100, pp. 131–138, 1978.

Silkoff, P. et al., "A technique to minimise the contribution of nasal nitric oxide to that measured at the mouth in humans;" The American Journal of Respiratory and Critical Care Medi 151(4):239, 1995.

Anggard, E.; "Nitric Oxide: mediator, murderer, and medicine; review article"; The Lancet; May 1994; vol. 343; No. 8907, p. 1199.

Borland, CDR., et al.,; "A simultaneous single breath measurement of pulmonary diffusing capacity with nitric oxide and carbon monoxide"; Eur Respir J; 1989, 2, pp. 56–63.

Brett, S.J. et al.; "Endogenous Nitric Oxide in Exhaled Human Breath"; Chest;110,4,Oct. 1996, p.873.

Fallat, R. et al.; "Distribution of Ventilation"; in Wilson, A.F., Editor, "Pulmonary Function Testing Indications and Interpretations"; Pulmonary Function Testing Indications and Interpretations; Grune & Stratton, Inc. (1985).

Guenard, H. et al.; "Determination of lung capilary blood volume and membrane diffusing capacity in man. . . "; Respiration Physiology (1987) 70, pp. 113–120.

Gustafsson, L.E.; Endogenous Nitric Oxide is Present in the Exhaled Air of Rabbits, Guinea Pigs and Humans; Biochem. and Biophys. Res. Com. vol. 181, No. 2, Dec. 16, 1991; pp. 852–857.

Hills, E.A. et al.; "Membrane diffusing capacity and pulmonary capillary volume in rheumatoid disease"; Thorax 1980 Nov.; 35 (11); pp. 851–855.

Husain, Mansoor et al.; Exhaled Nitric Oxide as a Marker for Organic Nitrate Tolerance; Circulation, vol. 89, No. 6, Jun. 1994, #2498 on p. A19.

Kharitonov, S.A. et al.; "Increased nitric oxide in exhaled air of asthmatic patients"; The Lancet; vol. 343 (Jan. 15, 1994), pp. 133–135.

Kilbourn, R.G., et al.; "Endothelial Cell Production of Nitrogen Oxides in Response to Interferon. . . "; HHS; NCI, J Natl Cancer Inst., May 2, 1990; pp. 32–38.

Leone, A.M. et al.; "Nitric Oxide is Present in Exhaled Breath in Humans. . . "; Biochemical and Biophysical Research Communications; vol. 201, No. 2, 1994, pp. 883–887.

Lundberg, Jon, "Airborne Nitric Oxide: Inflammatory Marker. . . "; Acta Physiologica Scandinavica Supplementum 633; Stockholm 1996; pp. 1–27.

Manicatide M.A. et al.; "Breathlessness and transfer factor for the lung. . . "; Rev. Roum Med Intern 1975; 13(1); pp. 53–57 (Abstract Only).

Meyer, M.et al.; "Nitric oxide (NO), a new test gas. . . "; Eur Respir J., 1989, vol. 2, pp. 494–496.

Moinard, J.et al.; "Determination of lung capillary blood volume and membrane diffusing capacity. . . "; Eur Respir J; 1990, 3, pp. 318–322.

Moncada, S.; "Nitric Oxide"; Journal of Hypertension; 1994, 12 (Suppl. 10); pp. S35–S39.

Morrison, D.et al.; "Reduced Exercise Capacity of Chronic Obstructive Pulmonary. . . "; The American Journal of Cardiology; vol. 64; Nov. 15, 1989, pp. 1180–1184.

Nathan, Carl F., et al.; "Does Endothelium–Derived Nitric Oxide Have a Role in Cytokine–Induced Hypotension?"; Journal of National Cancer Institute; May 2, 1990, 82: pp. 726–728.

Persson; Magnus G. et al.; "Single–breath nitric oxide measurements in asthmatic patients and smokers"; The Lancet; vol. 343 (Jan. 15, 1994).

Persson; M.G. et al.; "Endogenous nitric oxide as a probable modulator. . . "; Acta Physiol Scand 1990, 140; pp. 449–457.

Scheideler, L., et al.; "Detection of Nonvolatile Macromolecules. . . "; Am Rev Respir Dis., vol. 148; 1993; pp. 778–784.

Sherman, M.P. et al.; "Cytokine– and Pneumocystic carinii– induced L–arginine oxidation. . . " J Protozool 1991 Nov.– Dec.; 38 (6); pp. 234S–236S (Abstract Only).

Silkoff, P.E. et al., "Marked Flow–dependence of Exhaled Nitric Oxide. . . ", American Journal of Respiratory and Critical Care Medicine; vol. 155; 1997, pp. 260–267.

Swenson, E. et al.; "Conducting airway gas exchange: diffusion–related differences in inert gas elimination"; Airway Gas Exchange; 1992; pp. 1581–1588.

Vane, John R. et al.; "Mechanisms of Disease, Regulatory Functions. . . "; New England Journal of Medicine; Jul. 5, 1990; 323: pp. 27–36.

Yoshida, K. et al.; "Biotransformation of Nitric Oxide, Nitrite and Nitrate"; Int. Arch Occup Environ Health (1983) 52:103–115.

Yoshida, K. et al.; "Biotransformation of Nitric Oxide"; Environmental Health Perspectives; vol. 73, pp. 201–206 (1987).

METHOD AND APPARATUS FOR THE MEASUREMENT OF COMPONENTS OF EXHALED BREATH IN HUMANS

The present application is a continuation-in-part of application Ser. No. 08/629,594 filed Apr. 9, 1996, now U.S. Pat. No. 5,795,787, and is also based on Provisional Ser. No. 60/017,251 filed May 10, 1996, the disclosures of both parent applications being hereby incorporated by reference in their entireties.

FIELD OF THE INVENTION

This invention relates to the measurement of components of exhaled breath from the lower respiratory tract without contamination from substances originating in the upper respiratory tract, such as the nasal cavity, while controlling expiration at a fixed flow rate using biofeedback.

BACKGROUND OF THE INVENTION

The diagnosis of diseases through analysis of human breath has long been practiced in medicine. For example, by smell alone, various volatile components of breath such as acetone, ammonia or sulfur compounds can be detected and provide information used to evaluate conditions such as diabetes, liver impairment and kidney disfunction. Gas chromatography and mass spectrometry also have been applied to evaluate exposure to toxic substances, liver disease and lung cancer.

Thus, the measurement of exhaled substances may be useful as a diagnostic and prognostic tool in a variety of medical conditions for a wide variety of medical conditions. Often, it is of interest when assessing pulmonary function to measure one or more of a variety of exhaled substances. These include endogenous gases (ie., oxygen, carbon dioxide and nitric oxide), exogenous gases used to test pulmonary diffusing capacity (ie., carbon monoxide, acetylene, argon and helium), volatile substances (i.e., ethane and pentane) and non-volatile substances (i.e., proteins such as surfactants, DNA and hydrogen peroxide) often found by sampling the liquid present in exhaled breath (i.e., breath condensate).

For example, the detection of several non-volatile macromolecules in exhaled breath has been evaluated as a possible diagnostic tool. However, identical molecules may also arise in the nasal passages. See, generally, Scheideler et al., *Am. Rev. Respir. Dis.* 148:778–784 (1993). Thus, proteins in breath condensate have been collected and separated by two-dimensional polyacrylamide gel electrophoresis. Such samples were analyzed by immunoassay for inflammation related proteins such as interleukin-1, interleukin-2, tumor necrosis factor $\alpha$, and others. Id. The level of leukotriene B4, a mediator of mucosal inflammation, was found to be elevated in the breathing condensate of patients with bronchopulmonary disease. Becher et al., *App. Cardiopulmonary Path.* 5:215-219 (1995). Similarly, various compounds have been found to be elevated in patients with bronchogenic carcinoma. See, e.g., U.S. Pat. No. 4,772,559 to Preti et al. Also, the detection of pathogenic microorganism DNA in the airways has been evaluated by detecting isolated DNA in human exhalate. Hillebrand et al, *ATS Abstracts* (1996):181.

As another example of the importance of monitoring the components of exhaled breath, patients with stable and unstable chronic obstructive pulmonary disease exhibit increased oxidant production in the airways, increasing further during exacerbations, and levels can be monitored by measuring exhaled hydrogen peroxide. See, e.g., Dekhuijzen et al, *M. J. Resp. & Crit. Care Med.* 154:813–816 (1996). Thus, the measurement of exhaled hydrogen peroxide is a marker fox acute airway inflammation in pediatric asthma patients. Dohlman et al, *M. Rev. Resp. Disease* 148:955–960 (1993).

One exhaled substance of particular interest is exhaled endogenous nitric oxide (NO). Nitric oxide is now known to be a central mediator in biological systems and, therefore, endogenous exhaled nitric oxide is thus potentially of interest in the diagnosis and monitoring of pulmonary function and various pulmonary diseases. Nitric oxide can be measured in the exhaled breath of animal and human subjects and shows particular promise as a diagnostic tool useful in evaluating inflammatory airway diseases, in particular bronchial asthma, and also in evaluating bronchiectasis and lung transplant rejection and other pulmonary conditions. A recent article coauthored by the present inventors summarizes published values and techniques for measuring exhaled nitric oxide. See, Silkoff et al., *Am J. Resp. Crit. Care Med.* 155:260–267 (1997) and the references cited therein as well as Table 1, below.

For example, asthmatic patients have relatively high exhaled NO levels as compared to normal subjects and these levels decrease rapidly after the institution of anti-inflammatory therapy. See, e.g., Kharitonov, et al., *Lancet* 343:133–135 (1994). Thus, measuring exhaled NO in conjunction with existing tests may aid in the diagnosis and assessment of asthma, and also be an index of the response to therapy, or patient compliance in therapy. In view of the importance of asthma as a major health problem, the commercial potential is great for tests that can help diagnose assess severity and ascertain the response to therapy.

A variety of systems have been developed to collect and monitor exhaled breath components, particularly gases. For example, U.S. Pat. No. 3,951,607 to Fraser describes a gas analyzer for pulmonary use that is connected to appropriate detectors for, e.g., nitrogen, oxygen, carbon dioxide, carbon monoxide, helium, acetylene, nitrous oxide, nitric oxide, sulphur dioxide and anesthetic gases. Various other apparatus for collecting and analyzing expired breath include the breath sampler of Glaser et al, U.S. Pat. No. 5,081,871; the apparatus of Kenny et al, U.S. Pat. No. 5,042,501; the apparatus for measuring expired breath of infants of Osborn, U.S. Pat. No. 4,202,352; and the instrument for parallel analysis of metabolites in human urine and expired air of Mitsui et al., U.S. Pat. No. 4,734,777. Pulnonary diagnostic systems including computerized data analysis components also are known, e.g., Snow et al., U.S Pat. No. 4,796,639. Some detection systems rely upon mass spectrographic equipment and others rely upon rapid-response chemiluminescent analyzers such as Sievers Instruments, Inc. (Boulder, Colo.) Model 270B, which is preferred for the measurement of exhaled nitric oxide.

Notwithstanding the various known breath collection and analysis systems, published methods to date may be confounded by two problems. First, in order to measure the amount of substances originating from the lower respiratory tract as opposed to the upper respiratory tract (i.e., the paranasal sinuses and nasal cavities), a more informative system must substantially eliminate or exclude such substances to the extent that they originate from the upper respiratory tract, i.e., above the velum (or soft palate). For example, nitric oxide emerging from the nasal cavity is present in high concentrations relative to the level of nitric oxide originating in the lower respiratory tract, often in the parts per million range, and thus is present at levels that are an order of magnitude greater than those in the airways below the glottis. Such nasal cavity nitric oxide enters the airstream via the nasopharynx and then emerges through the mouth, and it preferably should be excluded. The present inventors have found that apparatus utilizing, e.g., a nose clip and low resistance mouthpiece, such as are used to monitor exhaled gases during exercise, are not adequate to satisfy the foregoing concern. Such a system is described, e.g., by Morrison et al., Am. J. Cardiol. 64:1180–1184 (1989).

Second, when measuring exhaled NO, for example, concentrations are altered (i.e., almost 35-fold) greatly by the expiratory flow rate, likely by affecting the transit time in the airway. The expiratory flow rate changes the transit time in the airway and thus changes the time available for NO uptake. Moreover, different people breath at different rates. Thus, a means for providing even and consistent flow rates also are important.

What has been needed, therefore, is a technique and associated equipment for receiving, collecting and sampling the components of exhaled breath in which contamination with substances present or originating in the upper respiratory tract, e.g., the nasal cavity, such as those originating from the nasal mucosa, is prevented or substantially reduced. Additionally, because an uncontrolled expiratory flow rate may complicate the measurement and evaluation of samples, techniques and methods to compensate for and substantially reduce variability also have been needed. The present invention thus is directed to such techniques and to associated equipment. Methods according to the invention are eminently suitable for both the inpatient and outpatient setting. The disclosed methods are reproducible, quick and easy to perform by medical staff and comfortable for the subject so that a pulmonary exhaled breath measurement system could become a routine part of the lung function assessment in every respirology clinic.

SUMMARY OF THE INVENTION

The present invention provides a method for measuring components of exhaled breath of a subject. The invention method includes the steps of causing the subject to exhale into an appropriate apparatus for receiving exhaled breath, increasing the pressure in the mouth of the subject to a level sufficient to cause the muscular closure of the soft palate (i.e., the velum) by the subject to isolate the nasopharynx during exhalation, and measuring the level of one or more components of the collected exhaled breath. A similar closure occurs naturally when, for example, playing a wind instrument or blowing up a balloon. The closing of the velum can be confirmed by concurrent monitoring of nasal $CO_2$ levels during exhalation which increase when the velum opens because of $CO_2$ originating in the lower respiratory tract.

Preferably, the method measures nitric oxide. However, a variety of other components of exhaled breath can be measured, including carbon dioxide, oxygen, nitric oxide, nitrogen, nitrogen dioxide, hydrogen peroxide, proteins, surfactants, DNA, acetone, ammonia, sulfur compounds, acetylene, carbon monoxide, ethane and pentane. For purposes of the present invention, the component of exhaled breath to be measured substantially arises from the respiratory tract below the glottis. Preferably at least about 75% of the components of exhaled breath are excluded, more preferably at least about 85% and most preferably at least about 95% of components originating in the upper respiratory tract are eliminated. (See Table 2. )

The method optionally may include the additional step of collecting one or more components of exhaled breath prior to measuring selected components. Preferably, the method includes the step of maintaining a constant flow rate of the exhaled breath of the subject This constant flow rate may be accomplished by a resistance means associated with the apparatus to receive exhaled breath, such as by associating or incorporating including a means for increasing resistance to the exhalation. Preferably the constant flow rate is effected by providing the subject who is exhaling breath with an instantaneous display of the pressure of the exhaled breath and the subject adjusts the force of the exhalation to maintain a constant pressure. The constant pressure and fixed resistance cause the expiratory flow to stabilize, and thus there is a steady NO uptake into the airflow and a NO plateau is observed, representing steady conditioning of the airflow with bronchial NO.

The invention apparatus provides a device for measuring components of exhaled breath of a subject in the methods described above. This device includes conduit means for receiving the exhaled breath from the subject, a means for increasing the pressure in the mouth of the subject to a level sufficient to cause the velum to close and thus to isolate the nasopharynx during exhalation, and a means for measuring the level of one or more components of the received exhaled breath.

This device preferably includes a means for providing the subject with an instantaneous display of the pressure of the exhaled breath so that the subject can adjust the force of the exhalation to maintain a constant pressure. Preferably, also, means for increasing pressure in the, subject's oral cavity (e.g., mouth and associated portions of the throat) are sufficient to increasing the pressure so as to substantially exclude the presence of components of exhaled breath arising from the nasal tracts and sinuses above the glottis.

BRIEF DESCRIPTION OF THE DRAWING FIGURES

This and other advantages of the instant invention will be more fully and completely understood by reference to the following description of the following drawings of an exemplary embodiment of the invention in which:

FIG. 1 shows a schematic diagram of an apparatus according to the present invention.

FIG. 2 shows a sample tracing of simultaneous nasal $CO_2$ recording (tracing A) and exhaled NO profile (tracing B). Arrows mark the point of mouthpiece insertion. The subject was told to swallow (S) showing the rise in $CO_2$ and the fall in $NO_{PLAT}$ as the velum opens.

DETAILED DESCRIPTION OF THE PREFERRED EMBODIMENT

Figure 1:
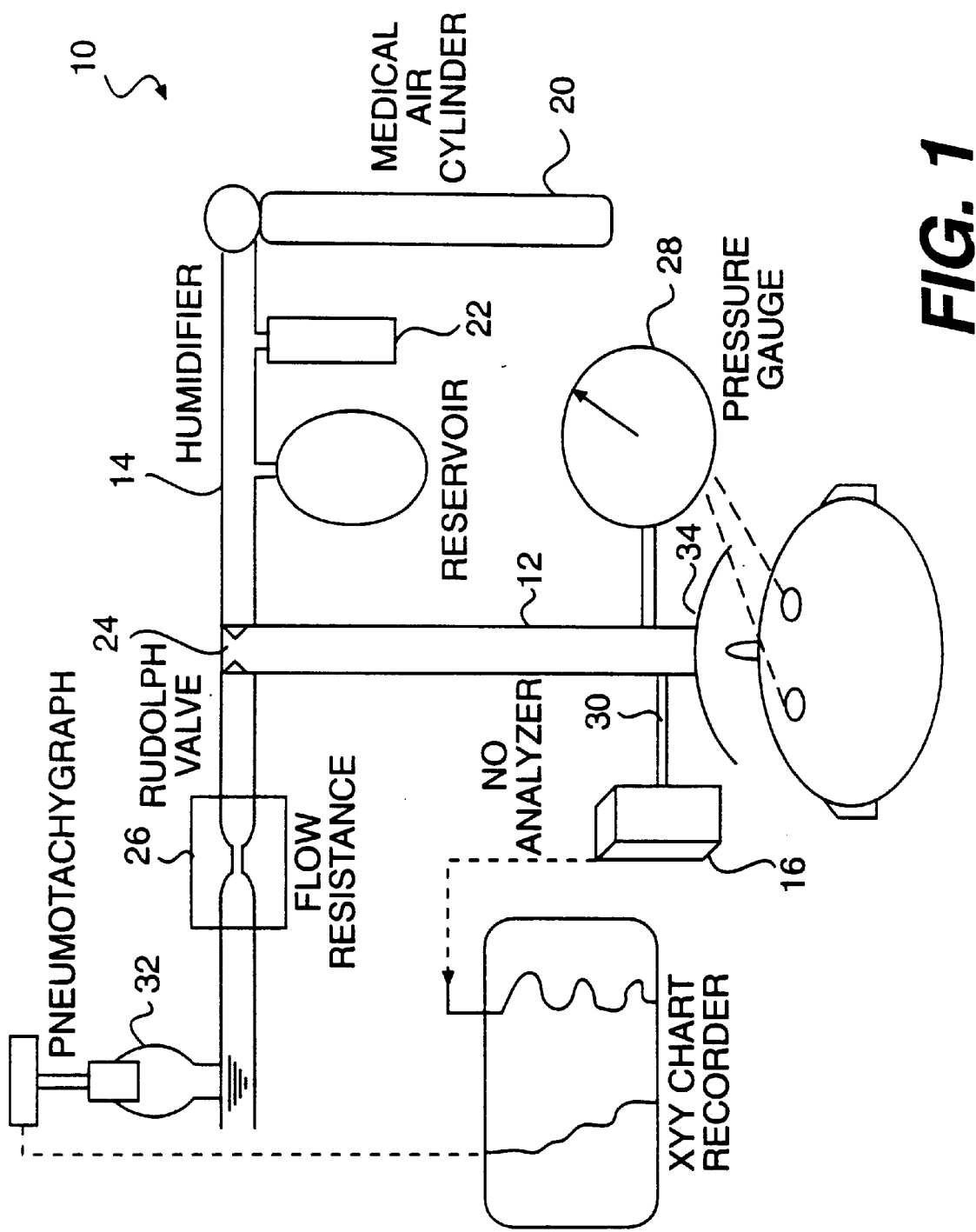

In a preferred embodiment of the present invention, positive mouth pressure is used to cause the subject to close the velum, thus excluding entrainment of nasal substances, e.g. NO. Also, one or more low standardized flow rates (e.g. 20 or 40 ml/s) preferably are used by introducing fixed expiratory resistances into the expiratory limb of a test circuit. This portion of the "test circuit" would comprise the "receiving" portion of the apparatus used to receive or collect exhaled breath.

The relatively low flow rates identified above amplify the concentration of substances arising in the lower airways, e.g., NO, thereby providing a more reproducible measurement of the exhaled breath of any subject and would allow greater differentiation between health and disease to the extent that particular levels of various exhaled substances or changes in the exhaled levels of such substances over time for any individual subject can be correlated with disease or impairment. Such techniques also would help to avoid the lower detection limits of the present day analyzers which are inaccurate. The disclosed methods also permit direct, valid, in the subject or intersubject or post-therapeutic comparisons. It is possible however to measure at any flow rate by varying the pressure/flow characteristics of the breathing circuit, according to specific clinical needs, e.g., of children, as long as the configuration of such embodiments is kept constant. There are not yet any standardized configurations or established guidelines for measuring exhaled NO. However, once a particular configuration has been designed, that embodiment should provide reproducible results, such as the NO plateau described in detail below. Note that the production of various low flow rates are only possible with fixed expiratory resistance.

According to a preferred embodiment of this invention, an apparatus for measuring substances, e.g., NO exhaled from the lungs of a subject or person, comprises conduit means for receiving the air exhaled by the person, means for increasing the pressure in the mouth of the person during exhalation to close the velum and thereby to isolate the nasopharynx and nasal cavity and to maintain a substantially constant flow rate of the air exhaled by the person, and measuring means for measuring the specific substance of interest, e.g., NO concentration in the exhaled air. Optionally, the apparatus includes the monitoring of nasal $CO_2$ to ensure velum closure.

The means for closing the velum may comprise resistance means in the conduit for reducing the flow rate of air exhaled by the person and pressure measurement and display or feedback means for assisting the person to maintain the air exhaled by the person at a relatively constant pressure. The pressure measurement means, for example, may include means for instantaneously displaying the pressure in the conduit so that the subject can adjust the force of his or her exhalation to maintain a constant pressure in the conduit.

Most subjects can maintain a consistent pressure within about ±10%, more preferably within about ±5%, has been found to be adequate to ensure precision and reproducibility. While a pressure of about 5 mm Hg is adequate to close the velum, we have found that about 20 mm Hg is easier for a subject to maintain while the exhalation remains comfortable to the subject Also, if a subject varies pressure slightly, a variation of ±1 mm at 5 mm pressure represents a 20% divergence while a ±1 mm Hg change at 20 mm Hg reflects only a 5% change. It is relatively easy to determine that the velum actually is closed by monitoring nasal $CO_2$ because measured $CO_2$ will increase substantially, approaching normal exhaled levels of $CO_2$ if the velum opens, and also the subject snorts and this can be heard by the operator of the relevant apparatus. Additionally if the velum is open, an initial NO peak will not be observed.

According to another embodiment of this invention, a method of measuring substances, e.g., NO exhaled from the lungs of a person, comprises increasing the pressure in the mouth of the person to close the velum and isolate the nasopharynx and to maintain a relatively constant flow rate of the air exhaled by the person. The concentration of the substance, e.g., NO concentration, in the exhaled air can be measured.

A flow rate in the range of about 40–80 mm per second is preferable. At this rate, there is enough amplification of the NO signal and to provide meaningful information. Because flow =pressure ÷ resistance, we prefer a precision of about ±10%, and ±5% more preferably. This precision would be adequate, and is the same as indicated above with respect to the pressure factor.

Abbreviations used in this specification include the following: NO: nitric oxide; $NO_{PLAT}$: plateau nitric oxide concentration; NOe: excretion rate of nitric oxide; TLC: total lung capacity; FRC: functional residual capacity; CV: coefficient of variation; rho: intraclass correlation factor; ANOVA: analysis of variance; PEEP: positive end expiratory pressure. References identified parenthetically by number are identified in a list that follows below, and all patents and journal articles identified anywhere in this specification are expressly incorporated by reference in their entireties.

Nitric oxide (NO) is a central mediator in biological systems (1, 2, 3), including the vascular endothelium (4), the immune system (1) and the non-adrenergic non-cholinergic nervous system (5). Endogenous exhaled nitric oxide is thus potentially of interest in the diagnosis and monitoring of various pulmonary diseases, including asthma (6, 7, 8). The single breath profile of exhaled NO concentration, performed while the subject wears a nose clip, has been described (9) as an initial NO peak followed by a NO plateau ($NO_{PLAT}$).

Peak NO values, $NO_{PLAT}$ values and mixed gas concentrations in collected air have all been used as parameters of pulmonary NO production (see Table 1). However, recent evidence suggests that a significant proportion of the NO in exhaled air originates in the nasal cavity (nose and nasopharynx) and that this accounts for the NO peak, with a lesser contribution from the lung (2, 9, 10). Reported values for exhaled NO vary greatly (Table 1) and the reasons for this have not been clear.

We reasoned that the wide variation in reported NO values (excluding studies on intubated subjects or tracheotomy samples) is primarily due to nasal NO contamination, as the velum may remain open during part or all of the respiratory cycle. The use of a nasal clip, which might be thought to solve the problem by encouraging oral airflow only, could also theoretically worsen the contamination not only by allowing nasal NO to accumulate, but also by causing velum opening (11). Secondly, the expiratory maneuvers employed in the published techniques vary greatly, most commonly consisting either of tidal breathing or vital capacity exhalations of various duration, each with its particular flow rate and flow pattern. Some investigators have reported that exhaled NO concentrations and NO excretion rates change with minute ventilation (12, 7, 13). In light of this, we proposed that another factor accounting for the variation in published NO values is the expiratory flow rate employed.

We set out to develop a technique for measuring exhaled NO of pulmonary origin that excludes nasal NO. Our approach makes use of high expiratory resistance to create a continuous, expiratory positive mouth pressure which closes the velum. By "high resistance," we mean resistance greater than about 400 cm $H_2O/l/sec$, more preferably in the range of about 600–1,200 cm $H_2O/l/sec$. With this technique, the early NO peak is absent in the single breath NO profile and there is a rapid rise in NO concentration to a plateau, representing alveolar air which has been conditioned by passage through the airways. This technique was then used to examine the relationship of $NO_{PLAT}$ to expiratory flow in ten healthy subjects (flow range 4.2 to 1550 ml/s). We found that $NO_{PLAT}$ levels and NO excretion rate (NOe) are markedly flow-dependent.

As shown in FIG. 1, apparatus 10 comprises conduit means 12, air supply conduit means 14 and NO analyzer means 16. Pursuant to the preferred embodiment, air having a defined concentration of any specific substance, e.g., NO, is supplied through a cylinder 20. By using air of a defined quality, the concentration of any substance, e.g., NO, as determined by the measurement obtained from the exhaled air may be normalized to take into account any amount of a specific substance, e.g., NO, which may be present in the feed air.

The air may be treated by a humidifier 22. Subsequently, the air travels through conduit 14 and conduit 12 for inhalation by the subject. The subject subsequently exhales into conduit 12. The air travels through conduit 12, past Rudolph valve 24 and subsequently through constriction 26 in the conduit. Constriction 26 causes an increase in pressure in conduit 12 and, accordingly, an increase in pressure in the mouth of the person who exhales. This increase in pressure is sufficient to close the velum, thus substantially excluding substances present or originating in the nasal cavity. An appropriate constriction can be made by using a standard 12 gauge or 18 gauge steel medical needle in the circuit. The actual flow can be measured to verify accuracy using standard techniques.

As the person exhales, the air may be sampled by an analyzer specific to the substance in question. Analyzer means 16 measures the level of the specific substance, e.g., NO, in the exhaled air. Pressure gauge 28 is in flow communication with conduit 12 and preferably provides an instantaneous measure of the pressure in conduit 12. During exhalation, the subject monitors the pressure in conduit 12 and adjusts the force of his or her exhalation to maintain the pressure, preferably, at the same level or, at least at substantially the same level, i.e., preferably with no more than about a ±5% variation.

To measure NO, for example, apparatus 10 may be used in conjunction with any commercially available rapid response NO analyzer. For the purpose of analyzing NO, the Sievers 270B (Boulder Colo) rapid chemiluminescent analyzer is preferred. For other substances, the receiving and collecting apparatus may be used with a rapid response analyzer appropriate for that substance and can such equipment routinely be selected by skilled artisans.

EXAMPLES

Example 1
Single Breath Profile of Exhaled Nitric Oxide.

The single breath profile of exhaled nitric oxide (eNO) (with nose clip) has been reported as an early NO peak (NOP) followed by a NO plateau (NOpl) which may correspond to lung NO. Recent evidence suggests that nasal nitric oxide (nNO) is high and gives rise to NOP.

NOpl was measured with a Sievers 270B analyzer. The measurement circuit consisted of a mouthpiece connected to a two-way non-rebreathing valve, through which the seated subject inhales humidified "medical air" (21% oxygen, balance nitrogen) from a reservoir. No nose clip was used. Ten healthy subjects inserted the mouthpiece, inhaled immediately to total lung capacity (TLC) and immediately exhaled. During the expiration, the subjects maintained a constant mouth pressure of 20 mm Hg, displayed to them on the dial of a pressure gauge, to close the velum thus excluding nNO (confirmed by nasal $CO_2$ probe). Nine separate flows were examined for NOpl for (4.2 to 1550 ml/s) using variable expiratory resistances.

NOP was absent with the 20 mm Hg mouth pressure. Ln(NOpl) fell linearly as LN(expiratory flow) rose (NOpl= $e^{(5^{727-0.5132(Ln(flow\ rate))})}$, R=0.808) with a more than 20-fold variation in mean NOpl (5.1±1.4 ppb to 112.5±54.89 ppb) as expiratory flow (EF) varied from 4.2 to 1550 ml/s. Ln NO excretion (NOpl×EF) however rose linearly with Ln EF. A 30 s breath hold produced the highest values of NOpl for all subjects (178.1±100.8 ppb). NOpl weal reduced at FRC as compared to TLC (about −20%, p=0.009) but was not affected by the level of expiratory pressure employed (20 mm versus 60 mm Hg, p=0.09).

Example 2
Profile of Single Breath Pulmonary Exhaled Nitric Oxide.

We measured pulmonary NO, without nasal NO, using positive expiratory mouth pressure (ensuring velum closure), and examined the variation in plateau NO over a range of expiratory flows (4.2 to 1550 ml/s). Plateau NO values rose almost twenty-fold (5.1±1.4 ppb to 112.5±54.8 ppb) with decreasing flow, described by NO plateau = $e^{(5.1727-0.5132(ln(flow\ rate)))}$. However, NO excretion showed an almost 17.5-fold rise as flow increased.

The disclosed technique therefore provide a simple method for measuring exhaled NO without the presence of significant levels of nasal NO. Notably, there is a marked flow-dependence of exhaled NO concentration and excretion. Based on the foregoing data, exhaled pulmonary NO is best measured at very low flow rates to amplify the NO concentration signal, and must be related to the expiratory flow employed.

Example 3
Apparatus for Measurement of Exhaled NO

1. Measurement of NO. A rapid-response chemiluminescent analyzer (Sievers 270B, Boulder, Colo.) with a response time <200 ms for 90% full scale was used. Calibrations to 350 ppb were performed using serial dilutions of a standard NO gas, and the analyzer sample flow rate was adjusted to 250 ml/min daily. The linearity of the analyzer response was verified by repeated calibrations. The manufacturer-specified lower limit of sensitivity for this analyzer is ~5 ppb; repeated calibrations with our instrument showed a lower limit of 2 ppb.

Nitric oxide was sampled close to the mouth via a sideport 30 (shown in FIG. 1). The total expiratory flow rate was taken as the sum of the analyzer flow and that measured by an expiratory pneumotachograph 32. Nitric oxide and flow signals were simultaneously displayed on an XYY chart recorder (Hewlett-Packard 7046A). The end point for the measurement was defined as a plateau ($NO_{PLAT}$) of at least 5 s duration. Three reproducible (±10%) $NO_{PLAT}$ tracings were recorded for each of the nine expiratory flows.

Lower respiratory NO excretion rate (NOe), the steady excretion rate occurring during the period of steady expiratory flow, was calculated from $NO_{PLAT}$ and flow rate according to the equation: $NOe(nmol/s) = NO_{PLAT}$ (ppb)×flow rate (ml/s)×k. The constant k=0.000040, and is a correction factor for STPD and conversion to nmol/s.

2. Selected Study Population. Healthy non-smoking volunteers 16 to 50 years old were recruited for the study. The research protocol was approved by the human ethics committee of The Toronto Hospital and carried out in accordance with the principles of the 1983 Helsinki declaration.

Example 4

Studies Performed to Validate the $NO_{PLAT}$ Technique

1. Determination of $NO_{PLAT}$ Using the High Resistance Technique (n=10).

The measurement circuit (FIG. 1) consisted of a mouthpiece 34 (as shown in FIG. 1) connected to a two-way valve, through which the seated subject inhaled humidified "medical air" (21% oxygen, balance nitrogen) from a reservoir. No nose clip was employed. Two separate pneumotachygraphs (Fleisch #1 and #3) were used to measure flow in the low and high ranges respectively and calibrated with known flow rates. Subjects performed nine exhalations at nine separate expiratory flow rates. Eight flow rates were determined using 8 resistances (R1 to R8). R1 was the resistance of the circuit alone. R2 and R3 consisted of short sections of inert tubing with internal diameters of 2 and 5 mm. R4 to R8 were created using standard medical needles (21, 20, 19, 18 and 16G). The ninth flow was that generated by the suction of the analyzer alone, with the expiratory limb occluded distal to the sample line. The nine flow rates thus achieved, were 1550, 850, 75.6, 38.2, 20.7, 17.2, 10.3, 8.5 and 4.2 ml/s. The highest possible flow at which the constant flow rate was maintained long enough to obtain a reliable $NO_{PLAT}$ was 1550 ml/s. For all flow rates, the subjects inserted the mouthpiece, inhaled immediately to total lung capacity (TLC) and immediately exhaled. During the expiration, subjects were asked to maintain a constant mouth pressure of 20 mm Hg displayed to them on the dial of a pressure gauge. The subjects achieved a good mouthpiece seal by supporting their cheeks and lips manually. Inflation of the cheeks was discouraged as this would be less likely to ensure velum closure.

2. Confirmation of Velum Closure During Expiration (n=5).

Vellum closure was assessed by monitoring $CO_2$ with a rapid response analyzer (Ametek, P61 B) via a probe in the anterior nares, while maintaining a constant mouth pressure of 20 mm Hg during the exhalations into the mouthpiece.

3. Study to Assess Nasal NO Leak with Intra-airway Sampling

In two healthy volunteers, after local anaesthesia with 4% lidocaine, a fine flexible catheter (8 and 10 gauge French) was passed via the nose and positioned in the trachea (confirmed by dysphonia) and withdrawn to 20 cm corresponding to the level of the vocal chords (continuing dysphonia). The placement was achieved in Subject 1 with a fiber optic laryngoscope. The presence of the catheter did not compromise velum closure. The NO analyzer sample line was connected via a three-way tap to the catheter and to the sideport of the mouthpiece. The subject then performed the NO measurements as described above at a flow rate of 20.7 ml/s. For each exhalation, the NO analyzer initially sampled at the mouth, and then once $NO_{PLAT}$ had been reached, was switched to sample from the catheter during the same exhalation maneuver. The same protocol was repeated with the catheter positioned in the oropharynx (confirmed by return of phonation) and additionally in the nasal cavity.

4. Studies to Assess the Influence of Inspired NO on $NO_{PLAT}$.

The purpose of these studies was to measure $NO_{PLAT}$ with a view to obtaining information about the underlying lung biology. However, $NO_{PLAT}$ might be affected by NO derived from the inhaled gas source, NO entrained during inspiration from the nasal cavity and NO taken up from the bronchial tree. Positive mouth pressure closes the velum to prevent nasal NO leak on expiration alone. Thus the velum may open on inspiration and nasal NO may be inspired. We performed two studies to determine whether $NO_{PLAT}$ is changed by deliberate NO inhalation.

5. Nasal Inspiration Compared to Mouth Inspiration (n=3)

$NO_{PLAT}$ was measured using the technique described above at a flow rate of 38.2 ml/s after inhaling via the mouth, and then measured in the same fashion immediately after inspiring the entire vital capacity through the nose in order to maximize nasal NO inhalation (three determinations).

6. Effect of High NO Inhalation(n=4)

$NO_{PLAT}$ was measured as described above, at a flow rate of 38.8 ml/s, after inhaling "medical air" via the mouth (three determinations). The subject then inhaled a high concentration NO mixture (~1 000 ppb) and $NO_{PLAT}$ was immediately measured (three determinations).

Example 5

Studies on the Exhaled NO Technique.

Five studies were performed to investigate the influence of expiratory flow, expiratory pressure, lung volume and intraday and interday variation on $NO_{PLAT}$.

1. Study to Assess the Variation of $NO_{PLAT}$ with Expiratory Flow

Subjects performed nine determinations of $NO_{PLAT}$ at nine separate expiratory flow rate. Two separate pneumotachygraphs (Fleisch #1 and #3) were used to measure flow in the low and high ranges respectively and calibrated with known flow rates. Eight flow rates were determined using 8 resistances (R1 to R8). R1 was the resistance of the circuit alone. R2 and R3 consisted of short sections of inert tubing with internal diameters of 2 and 5 mm. R4 to R8 were created using standard medical needles (21, 20, 19, 18 and 16G). The ninth flow was that generated by the suction of the analyzer alone, with the expiratory limb occluded distal to the sample line.

The nine flow rates thus achieved, were 1550, 850, 75.6, 38.2, 20.7, 17.2, 10.3, 8.5 and 4.2 ml/s. The highest possible flow at which the constant flow rate was maintained long enough to obtain a reliable $NO_{PLAT}$ was 1550 ml/s. Three reproducible (±10%) $NO_{PLAT}$ tracings were recorded for each of the nine expiratory flows. The total expiratory flow rate was taken as the sum of the analyzer flow and that measured by an expiratory pneumotachograph.

Lower respiratory NO excretion rate (NOe), the steady excretion rate occurring during the period of steady expiratory flow, was calculated from $NO_{PLAT}$ and flow rate according to the equation: $NOe(nmol/s)=NO_{PLAT}(ppb) \times$ flow rate (ml/s)×k. The constant k =0.000040, and is a correction factor for STPD and conversion to nmol/s.

2. Interday and Intraday Variation (n=6).

On 4 separate days, $NO_{PLAT}$ measurements at three separate flow rates (10.3, 20.7 and 38.2 ml/s) were made in the morning. In the same subjects, 4 measurements of $NO_{PLAT}$ were made during normal laboratory hours (9 a.m. to 5 p.m.) at two-hourly intervals at the same flow rates. In this study, only these 3 flow rates were selected to facilitate repeated measurements.

3. The Effects of Lung Volume (n=10).

This study was performed to assess the impact of incomplete inhalation to TLC as a possible source of error. Here, NO$_{PLAT}$ values measured from TLC were compared to those obtained from functional residual capacity (FRC) for three expiratory flows (10.3, 20.7 and 38.2 nml/s). For the FRC values, the subject inserted the mouthpiece after a period of quiet tidal breathing at the end of exhalation, and exhaled immediately into the mouthpiece while maintaining a mouth pressure of 20 mm Hg.

4. The Effects of Expiratory Mouth Pressure (n=5).

This study was performed to assess the impact of variation in the mouth pressure produced by the subject as a possible source of error. Nitric oxide plateau values obtained using an expiratory pressure of 20 mm Hg were compared to those obtained with a pressure of 60 mm Hg. Here, NO$_{PLAT}$ values were interpolated from the NO flow curves at five flow rate (15, 20, 25, 30 and 35 ml/s) as the flows with 60 mm Hg pressure were different from 20 mm Hg pressure for the same resistances.

5. Thirty Second Breath Hold Maneuver (n=10).

This study was performed to assess the impact of pausing between inspiration and expiration (breath hold) as a possible source of error and to examine the limits of NO accumulation within the airway. Subjects inhaled to TLC and sustained a mouth pressure of 20 mm Hg for 30 s against a closed valve (NO analyzer sample port closed). After 30 s the analyzer port was opened and the NO concentration was recorded.

Example 6

Statistical Methods.

Since the Shapiro-Wilk test suggested deviation from normal Gaussian distributions for the NO concentrations and the 9 flow rates, natural logarithm transformations were applied to both parameters, thus reducing skewness and kurtosis and the deviation from normal distributions. The relationship between ln(NO) and lN(Flow) was analyzed using least squares linear regression.

The descriptive statistics of within-day and between-day variation were the mean coefficients of variation (CV). The reproducibility of the within-day and between-day variation (as compared to between individuals variability) was assessed by extracting the intraclass coefficient of reliability (rho), which can range from 0 (no reproducibility) to 1.00 (perfect reproducibility).

The two levels of lung volume (TLC vs FRC) for the three expiratory resistances yielded a 2×3 repeated measures analysis of variance (ANOVA) for the scrutiny of the relationship of lung capacity and expiratory flow to NO concentrations. The two levels of expiratory pressure and the five flow rate examined yielded a 2×5 repeated measure ANOVA for the relationship of pressure and flow rates to NO$_{PLAT}$. For all tests, p<0.05 was used to ascertain statistical discernibleness.

Example 7

Studies Performed to Validate the NO$_{PLAT}$ Measurement Technique

1. Confirmation of Velum Closure

Figure 2A:
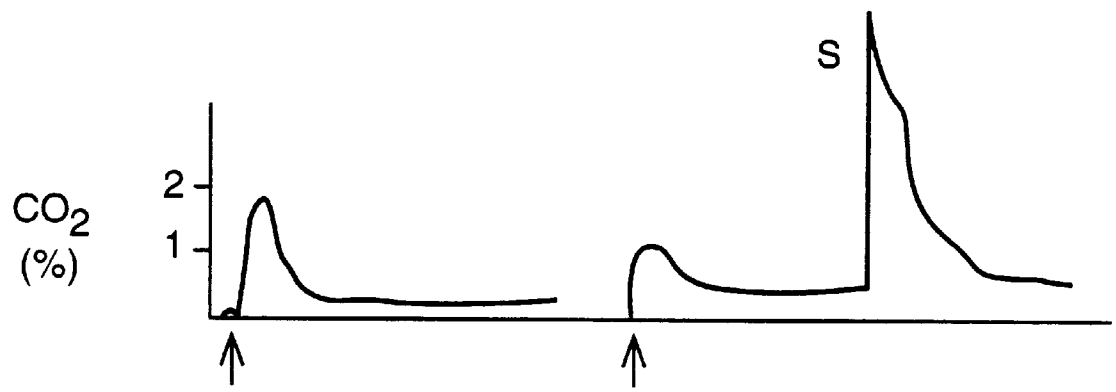
Figure 2B:
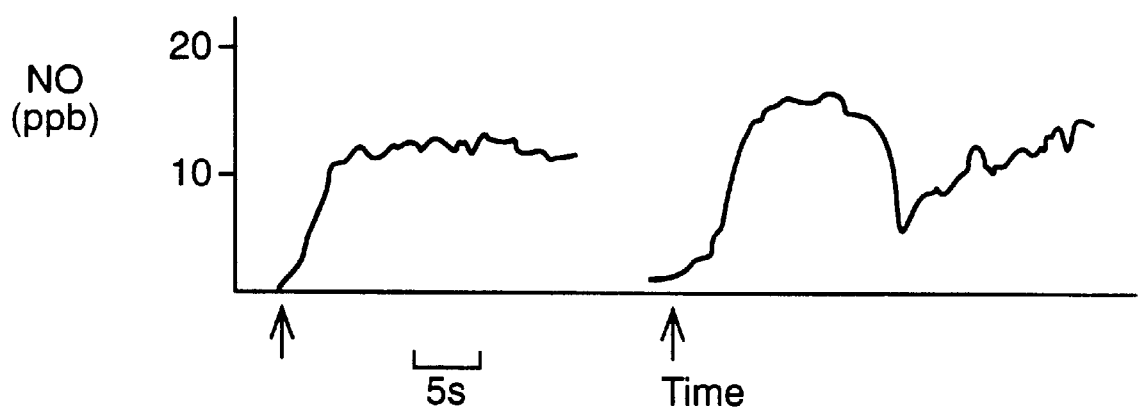

In five subjects, CO$_2$ monitoring in the nasal cavity during the exhalations showed that nasal CO$_2$ concentration, which was higher as the subject inserted the mouthpiece, fell to very low levels during the exhalation (~0.2%) thus indicating velum closure. FIG. 2 shows one tracing and the resultant peak (S) that occurred as the subject was asked to swallow and the velum opened. NO$_{PLAT}$ fell also, as the velum opened and gas escaped via the nose.

2. Comparison of NO$_{PLAT}$ at the Mouth With That Sampled in the Airway (n=2).

NO$_{PLAT}$ values sampled by catheter just below the vocal chords, in the oropharynx and in the nasal cavity are presented in table 2, and indicated that mouth and intra-airway values are equivalent. The levels of nasal NO recorded in the nasal cavity during the mouth exhalation were markedly higher than the airway values.

3. The Influence of Nasal NO Entrained During Inhalation (n=5)

Figure 3:
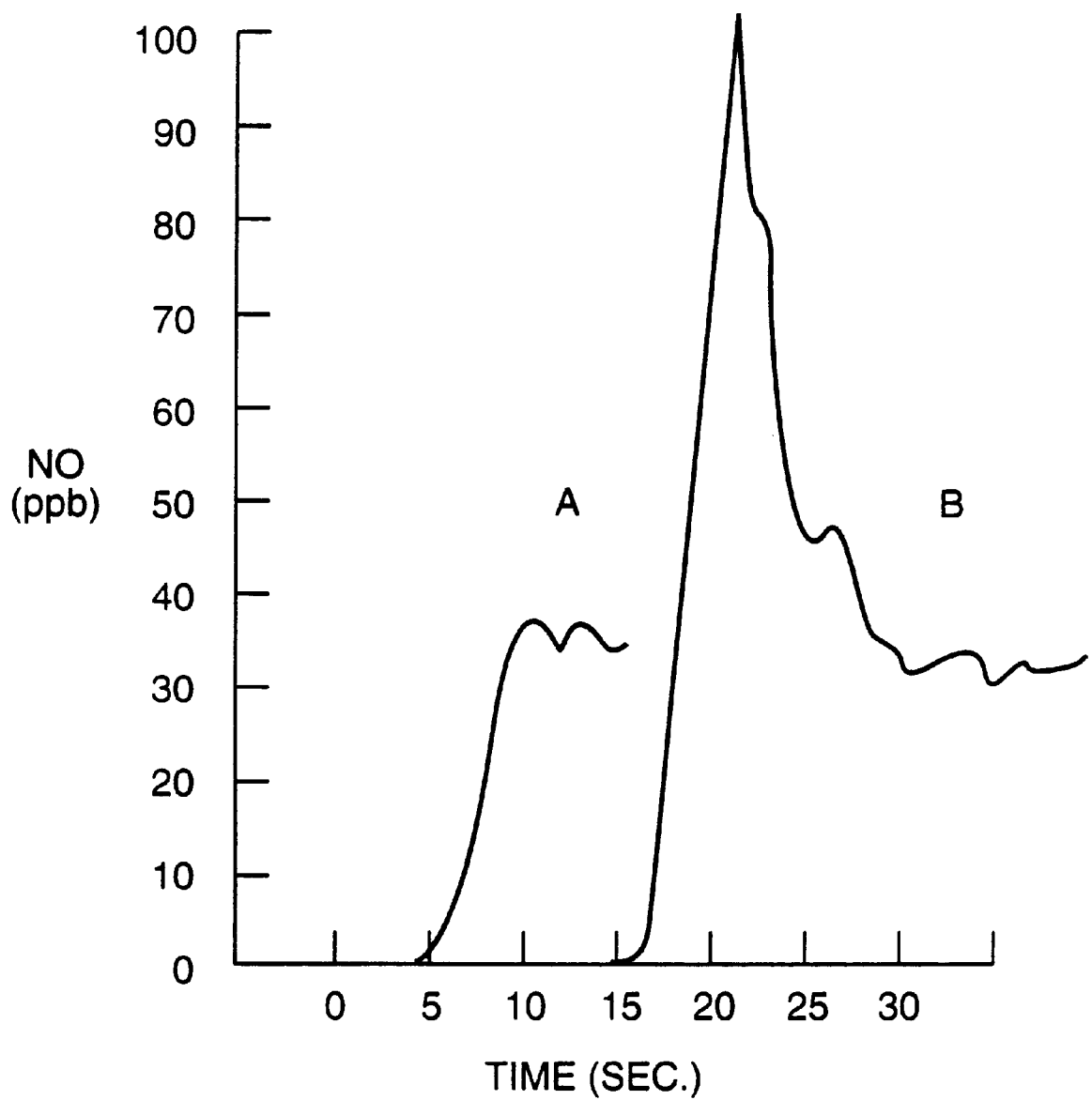
FIG. 3 shows a single breath NO profile by inhalation via the mouth (tracing A) compared with that performed after inspiration via the nose (tracing B).

Nasal inspiration(n=5) The exhaled NO profile after inhaling via the nose differed from that obtained by inhaling via the mouth (FIG. 3). There was a rapid rise and an initial peak which was then followed by a plateau (NO$_{PLAT}$). There was no significant difference between NO$_{PLAT}$ after mouth inhalations and after nose inhalations (14.6±4.4 vs 14.2±4.1 ppb).

4. The Influence of Inhaling a High Concentration NO Gas On NO$_{PLAT}$ (n=4).

The NO concentration of the inhaled gas was 1059±175.7 ppb. Similar to the previous study, the breath profile of exhaled NO changed after inhaling the high concentration mixture, showing a huge initial NO peak which then fell to a plateau (NO$_{PLAT}$). There was no significant change in NO$_{PLAT}$ after the high NO inhalation (18.9±7.0 to 16.6±4.0 ppb, p=0.22).

Example 8

Studies On the NO Measurement Technique

1. The Variation of NO$_{PLAT}$ With Expiratory Flow (n=10).

All subjects reported that the technique was generally comfortable and most agreed that this test was easier to perform than a standard forced expiration. With higher resistances the expiratory effort had to be maintained up to 36 seconds which caused mild discomfort for some subjects with occasional transient fatigue of the oral musculature. Three reproducible values (±0%) of NO$_{PLAT}$ for each resistance were achieved with 3–5 determinations in most subjects.

The tracing of NO$_{PLAT}$ demonstrated a rapid rise to a plateau (FIG. 4). The time to reach the plateau increased with increasing resistance and resultant decreasing expiratory flow rate (range 2.7–36 s for flows 1550–4.2 ml/s respectively). No early NO peaks were present when the 20 mm Hg mouth pressure was maintained.

Figure 4A:
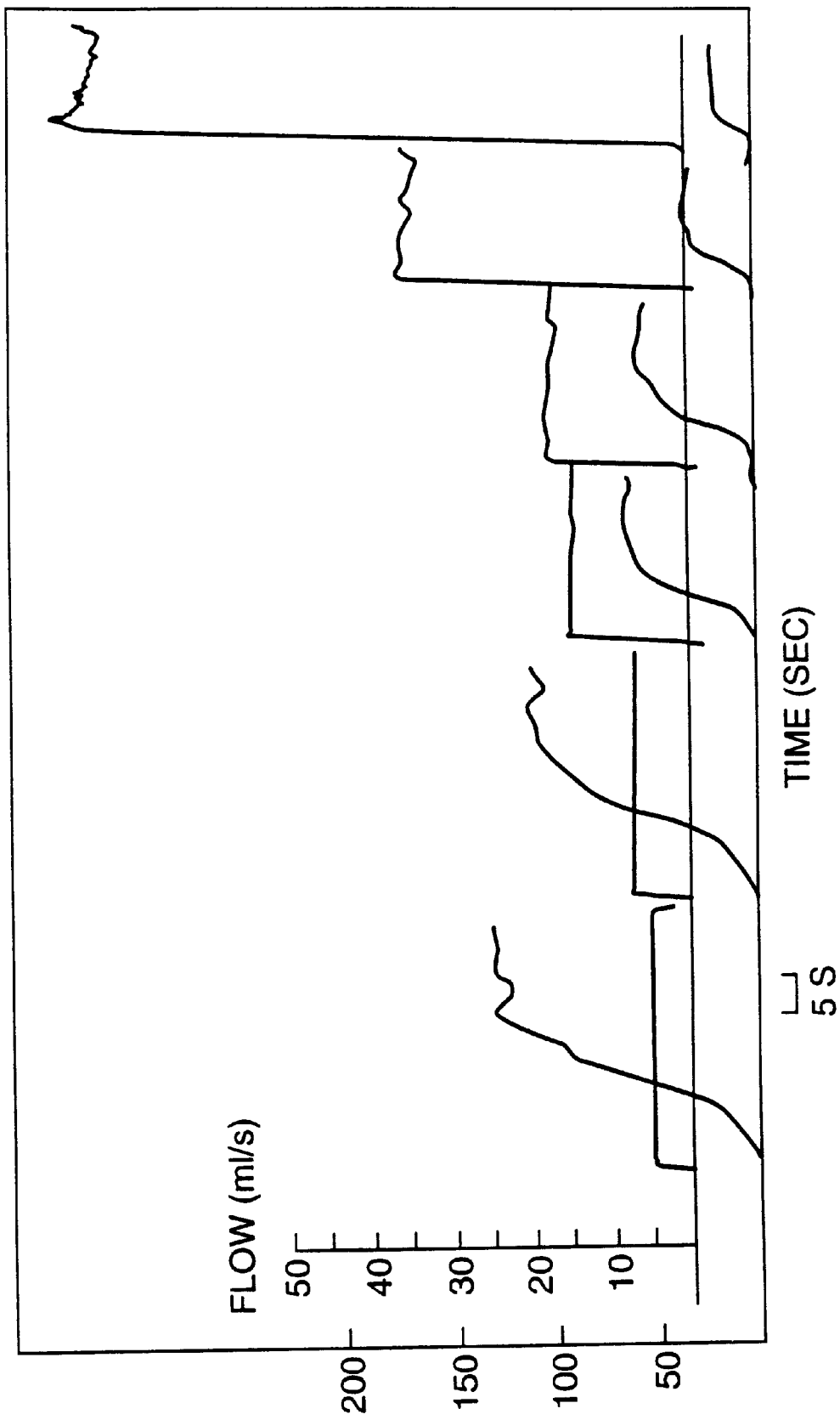
FIG. 4A shows tracings in one subject of $NO_{PLAT}$ and expiratory flow profiles for six resistances with flows from 8.5–75.6 ml/s.
Figure 4B:
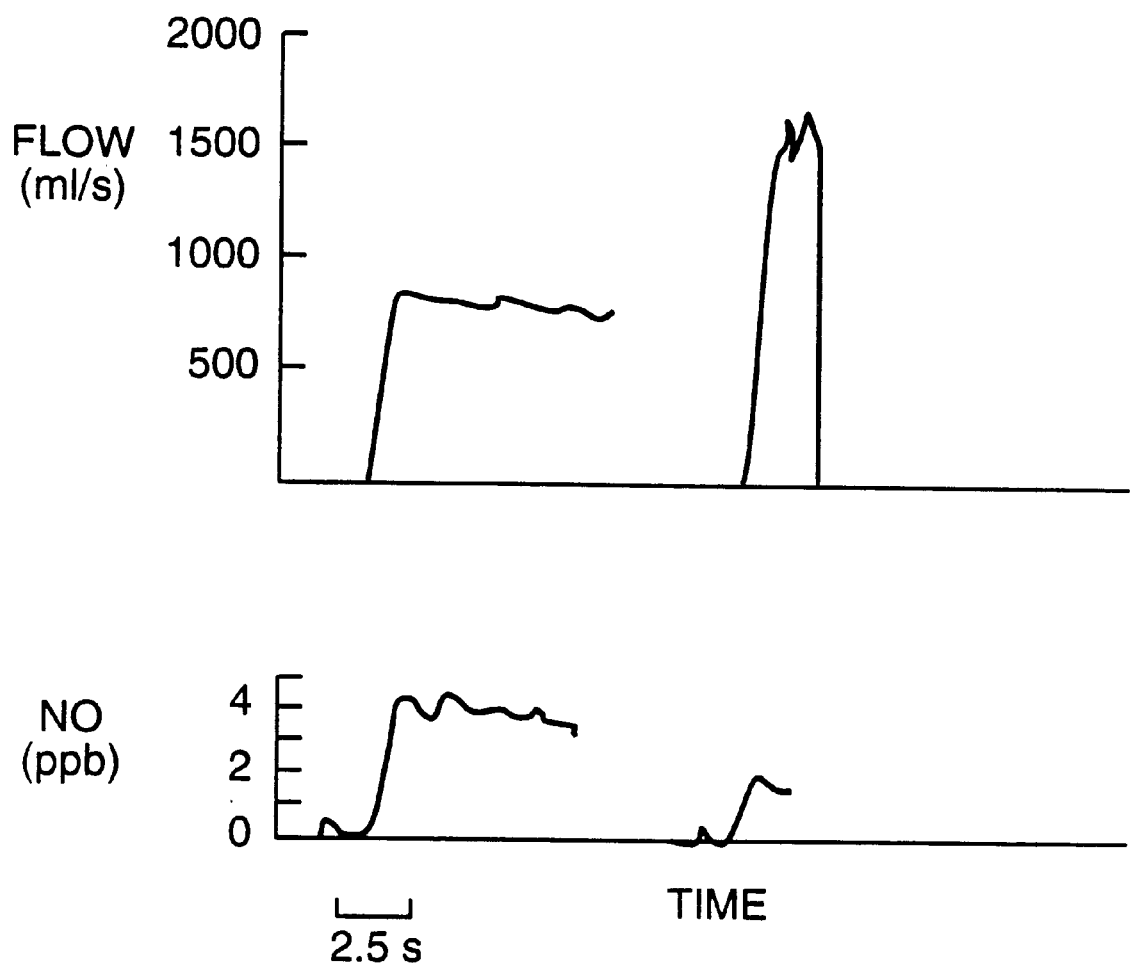
FIG. 4B shows simultaneous $NO_{PLAT}$ and expiratory flow profiles for two resistances with flows of 850 and 1,550 ml/s.
Figure 5A:
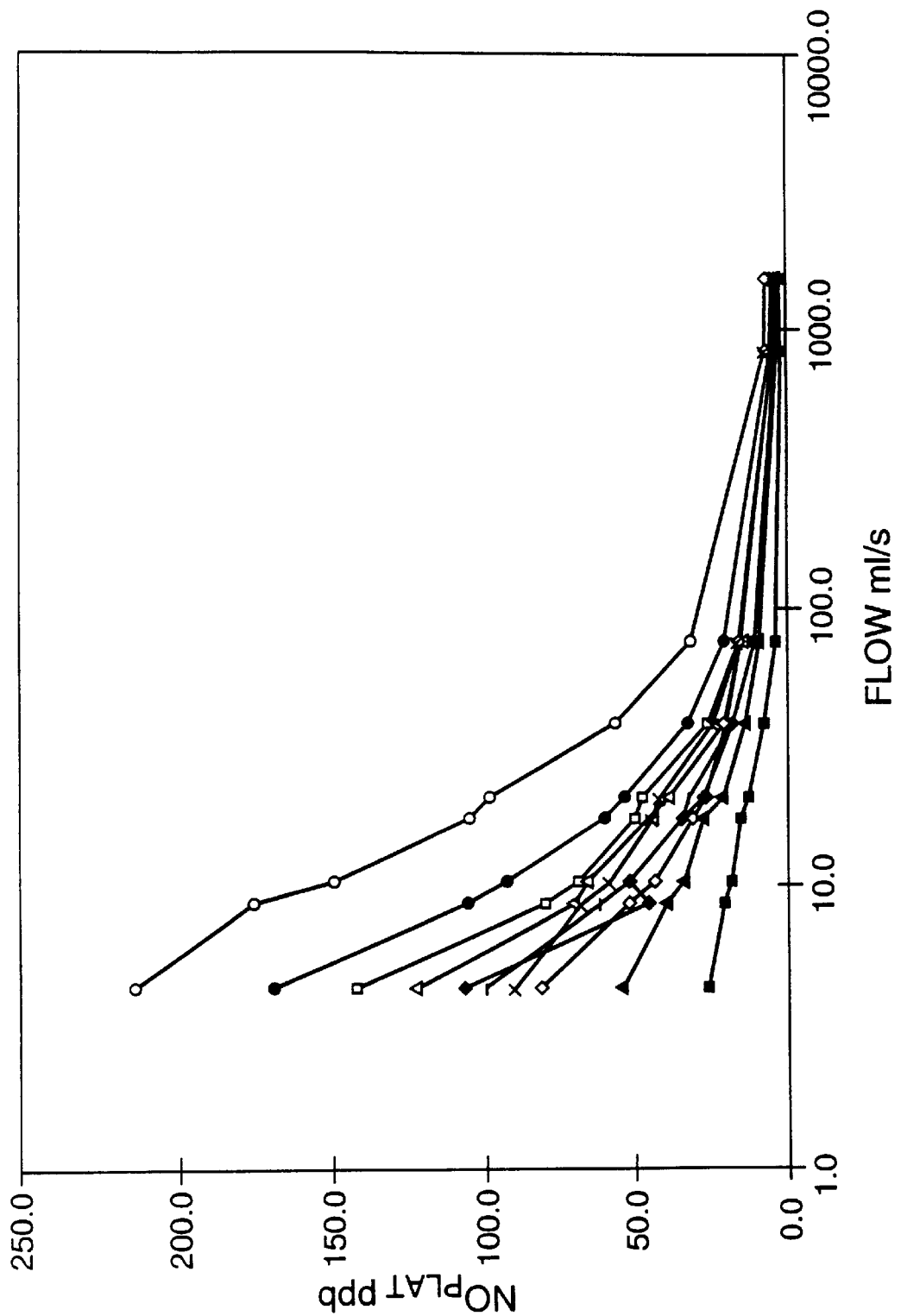
FIG. 5A shows the $NO_{PLAT}$ (ppb) versus log flow rate in 10 subjects.

In all subjects NO$_{PLAT}$ fell with increasing flow rates (FIGS. 4A). For each of the nine flows examined, there was a highly significant difference in the NO$_{PLAT}$ value. There was a more than twenty-fold increase in mean NO$_{PLAT}$ (5.1±1.4 ppb to 112.5±54.8 ppb, p=0.0001) for a 400-fold decrease in flow. The standard deviations showed that the distribution of NO$_{PLAT}$ values between subjects was narrow at high flow rates but widened markedly with decreasing flow rate (NO$_{PLAT}$ range 27.5–215.9 ppb at flow 4.2 ml/s). The relationship of NO$_{PLAT}$ to flow using natural logarithm-transformed data was well described (R$^2$=0.808, p=0.0001, FIG. 5A) by $$NO_{PLAT} = e^{(5.17270 - 0.5132(ln(flow\ rate)))}$$

Figure 6:
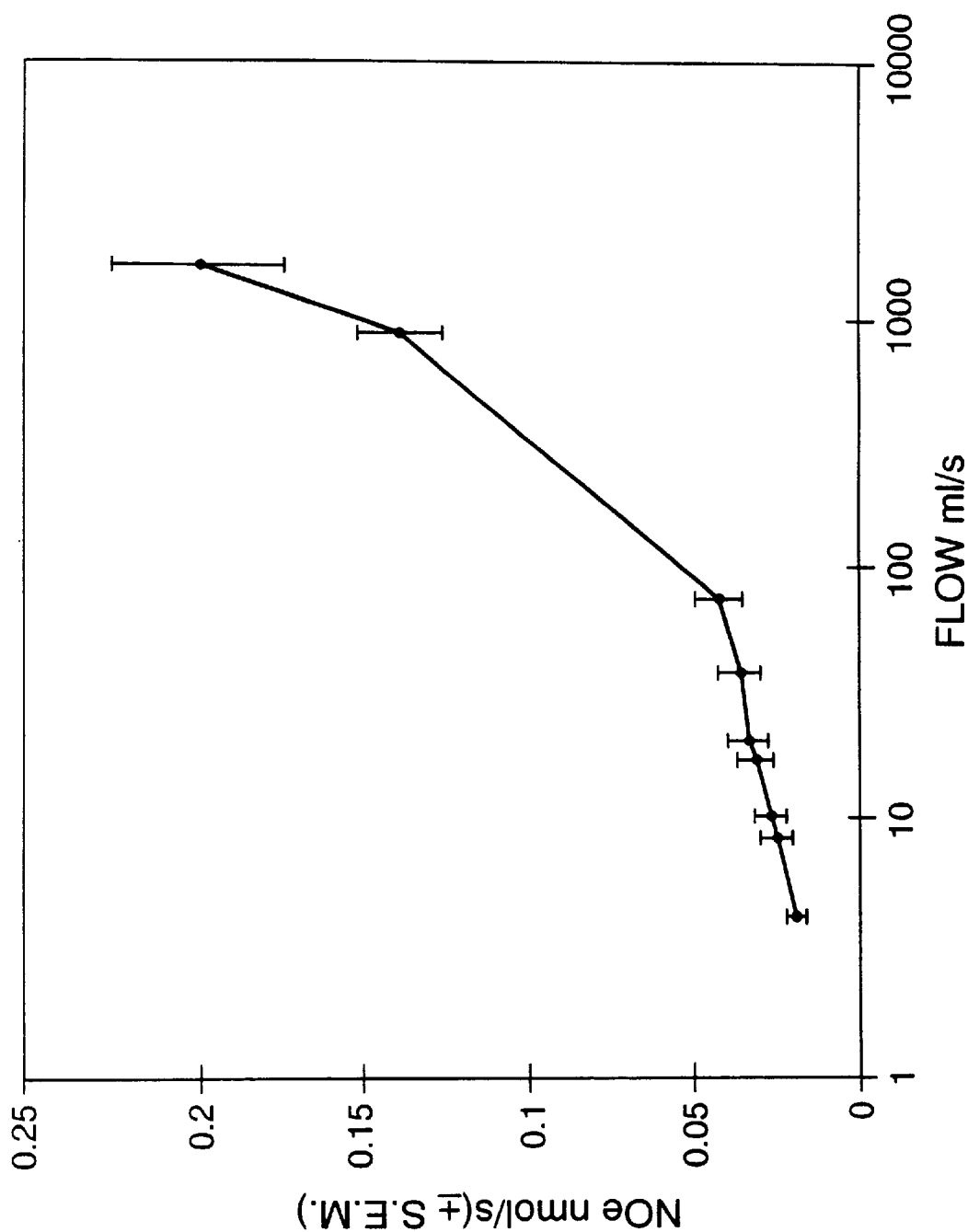
FIG. 6 shows NOe (mean±SEM, n=10) versus log flow rate in 10 subjects measured at nine resistances.
Figure 7:
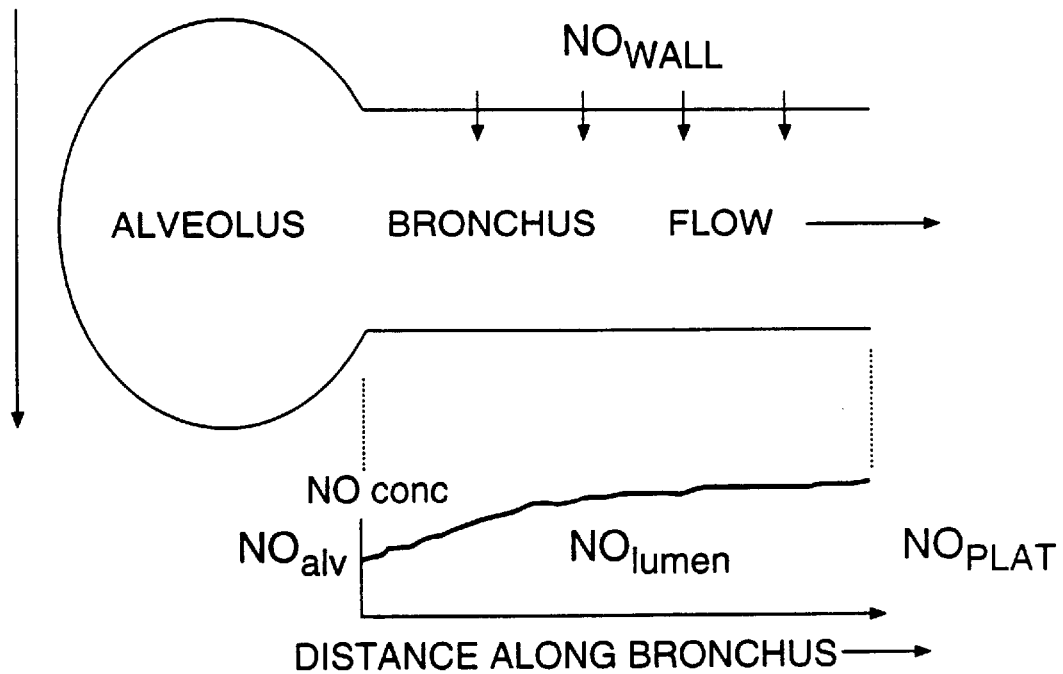
FIG. 7 shows a theoretical model of NO excretion showing schematic alveolus an airway, with expiratory flow and difflusion of NO from wall to lumen. The graph shows theoretical NO concentration at progressive points in the lumen under conditions of steady flow.

Nitric oxide excretion (derived from flow and NO$_{PLAT}$) was also flow-dependent, but in contrast to NO$_{PLAT}$, rose linearly as flow rate increased for all subjects (natural logarithm transformed data, FIG. 6). There was a 17.5-fold increase in NOe (0.0189±0.009 to 0.33052±0.087 nmol/s) as flow increased from 4.2 to 1550 ml/s.

2. Interday and Intraday Variation NO$_{PLAT}$ of (n=6).

The CVs and rho values for interday and intraday studies for the same subjects at three flow rates are presented in Table 3. The intraclass correlation (rho) for the three flow rates, indicate that there was good interday and even better intraday reproducibility. There was no systematic pattern in the variation of NO$_{PLAT}$ throughout the day.

3. The effects of lung volume on $NO_{PLAT}$ (n=10).

The values of $NO_{PLAT}$ obtained with exhalations from FRC were significantly less than those from TLC (by approximately 20%) for all three flow rates examined (p=0.0093, Table 4).

4. The Effects of Expiratory Pressure On $NO_{PLAT}$ (n=5).

Analysis of the effects of pressure at five separate flow rates showed that there was no significant difference between the $NO_{PLAT}$ levels measured with expiratory pressures of 20 and 60 mm Hg (p=0.0942, Table 4).

5. Breath Hold Values (30 s) and Fastest Exhalations (n=10).

Nitric oxide plateau values after a 30 second breath hold, the slowest exhalation (flow=4.2 ml/s) and the fastest exhalation (flow =1550 ml/s) are presented in Table 5. A 30 s breath hold maneuver produced the highest values of $NO_{PLAT}$ for all subjects (178.1±100.8 ppb).

Example 9
Exhaled Nitric Oxide (eNO) and Nitric Oxide Excretion Rate (exNO) Are Markedly Flow-Dependent. A Technique to Measure eNO Without Nasal Nitric Oxide (nNO).

Exhaled nitric oxide (eNO) may be of value in the monitoring of pulmonary disease. The single breath profile of eNO (with nose clip) was reported as an early NO peak (NOP) followed by a NO plateau (NOpl) maybe corresponding to lung NO. Recent evidence suggests that nNO is high and gives rise to NOP. Published values for eNO vary widely possibly due to the differences in the measurement techniques. Some techniques may allow nNO to enter the oral airflow and expiratory flow (EF) varies with the respiratory maneuver employed (e.g., tidal breathing versus vital capacity exhalation of varying speed). We measured NOpl with a Sievers 270B analyzer. 10 healthy subjects maintained a constant expiratory oral pressure (20 mm Hg) to close the velum thus excluding nNO (confirmed by nasal $CO_2$ probe) and we examined NOpl for 9 separate flows (4.2 to 1550 ml/s) using variable expiratory resistances.

RESULTS. NOP was absent with the 20 mm Hg mouth pressure. Ln(NOpl) fell linearly as Ln(EF) rose (NOpl=e$^{(5.17270-0.5132(Ln(flow\ rate)))}$, $R^2$=0.808) with a more than 20=fold variation in mean NOpl (5.1±1.4 ppb to 112.5±54.8 ppb) as EF varied from 4.2 to 1550 ml/s. Ln NO excretion (NOpl×EF) however rose linearly with Ln EF. A 30 s breath hold produced the highest values of NOpl for all subjects (178.1±100.8 ppb). NOpl was reduced at FRC as compared to TLC (±20%, p=0.009) but not by affected by the level of expiratory pressure employed (20 mm versus 60 mm Hg, p=0.09).

CONCLUSIONS. It is possible to measure eNO without nNO with our method. eNO is best measured at very low constant EF to amplify the signal. In view of the marked flow-dependence of eNO, measurement techniques must be related to the expiratory flow used.

Example 10
Exhaled Nitric Oxide After Inhaled Salbutamol and Ipatropium Bromide Using a Technique to Measure Lung NO Without Nasal NO.

Exhaled NO is of interest in the monitoring of subjects with asthma and other airway diseases. NO was measured with a new technique (abstract submitted jointly). Six healthy subjects inhaled to TLC and exhaled via a high resistance at a constant low expiratory flow rate (20.7 ml/s) while maintaining a continuous oral expiratory pressure (20 mm Hg) to close the velum thus excluding nasal NO (confirmed by nasal $CO_2$ probe). On three separate days, NO was measured before and after taking either 400 $\mu$ salbutamol (S), 80 $\mu$ ipatropium (C), or placebo (P) administered double-blind from a MDI inhaler by spacer. NO was measured at 15 minutes., 30 minutes, and then hourly for 4 hours. In a pilot study (n=6), the coefficient of variation in NO on repeated measures on a single day was ~10%.

RESULTS. With S, I and P, there was a tendency for mean NO to fall starting at 15 minutes, and reaching minimum values at 30 minutes (S: 0.84±0.15, I: 0.85±0.06, P: 0.91±0.13 of baseline). These small changes were not significant (p>0.19). Recovery of NO to baseline with P occurred by 60 minutes, with I by 120 minutes but with S, NO remained low for the total duration of the follow up. The mean change in FEV1 was 7% (S and A) and 2% (P).

CONCLUSIONS. This study shows that there is a tendency for NO to fall following the administration of S, I and P. with the small subject number there was no statistical significance but the time course and the difference in the profiles between S, I, and P suggests that there is a real effect. An effect of the inhaler propellant is possible. The mechanism of this fall is not clear but could include vasodilatation in the bronchial wall increasing NO uptake (S), or direct effect on NO synthetases. This study supports measuring NO at least 6 hours after prior bronchodilator administration.

DISCUSSION

In this study, we proposed and validated a technique for measuring exhaled NO which overcomes the problem of expiratory nasal contamination of the exhaled pulmonary gas. Using this technique, we present evidence that there is a striking variation in $NO_{PLAT}$ concentration and NOe, which occurred as the expiratory flow varied from 4.2–1550 ml/s. This finding has important implications for future studies of exhaled NO.

The study was initiated in order to explore mechanisms underlying the large variation in published values for exhaled NO (Table 1).

Firstly, we suspected that nasal NO, whose concentrations have been reported to be considerably higher as compared to exhaled NO (9, 14, 15), contaminates the expiratory airflow. In a preliminary NO study (16), performed with the subject using a nasal clip, we observed an early NO peak which we suspected arose in the nasal cavity, as nasal aspiration attenuated or abolished the NO peaks. Technical solutions to this issue of contamination from nasal NO have not been proposed to date.

Secondly, published measurement techniques vary greatly between investigators. Schilling et al (17) and Alving et al (6) employed tidal breathing, Kharitonoy et al (7) used a 3045 s vital capacity exhalation, while Persson et al (18, 19) used a 10–1 5 s vital capacity exhalation. Thus the expiratory flows and profiles would have varied correspondingly.

The possible importance of expiratory flow in the measurement of NO concentration and excretion has been reported by several investigators, who observed an influence of minute ventilation on exhaled NO, particularly in the setting of exercise hyperventilation (13, 12, 20). Tidal breathing in particular, is characterized by significant breath to breath variation in rate and volume, and there may be periodic variations in FRC which could theoretically alter NO levels, especially in asthmatic subjects. Other methodological differences include the use of a short breath hold before the exhalation (8) and the use of a nose clip. Massaro et al (22) state that the use of a nose clip ensured that the exhaled NO was of alveolar origin. However, the use of a nose clip may actually worsen the nasal NO leak, by allowing accumulation of nasal NO and by encouraging velum opening, as occurred in acoustic reflection studies(11). Similar to single breath analysis, gas collection techniques vary greatly in the respiratory maneuver employed. We wished therefore to measure orally-exhaled NO without the influence of nasal NO, and to examine the relationship of NO levels to expiratory flow as the main variable from technique to technique.

Our method employs continuous expiratory pressure to close the velum during exhalation to exclude nasal NO which may leak throughout exhalation in the presence of an open velum. We are confident that this was achieved, as a nasal $CO_2$ probe showed no expiratory rise in five subjects (FIG. 2). In any case, the maintenance of a constant positive expiratory mouth pressure without a nose clip is possible only with the velum closed. The absence of early NO peaks in the $N_{OPLAT}$ traces obtained with our technique, in contrast to exhalations performed with no expiratory resistance or pressure (9), also indicates that the velum is closed and confirms the nasal origin of the early NO peak. As can be seen in FIG. 2, if the velum opens, the $N_{OPLAT}$ is not maintained, and so the trace itself serves as a confirmation of velum closure.

Further validation was achieved through the comparison of sampling $N_{OPLAT}$ at the mouth to intra-airway measurements. In 2 subjects, the catheter NO levels at the glottis are in good agreement with those measured at the mouth. The small difference between mouth and catheter in subject 1 (<2 ppb) may be due to oropharyngeal NO production, and probably not nasal leak, as the extremely high NO levels measured above the velum would have grossly contaminated the mouth samples if the velum were open. This catheter study supports the tight closure of the velum and the prevention of expiratory nasal NO leak with the measurement technique. It also confirms that $N_{OPLAT}$ measured with this technique is of lower respiratory tract origin and not mainly nasal NO, as has been suggested (9).

The study of the influence of nasal inspiration on $N_{OPLAT}$ (the maximal introduction of nasal NO during inspiration) showed that although the NO profile was changed due to the dead space being fall of the nasal NO (FIG. 3), once the dead space gas was exhaled, $N_{OPLAT}$ was unchanged. Thus it is only necessary to assure velum closure during expiration. The same findings apply to the study where inhaling a gas with a relatively very high NO concentration did not change $N_{OPLAT}$. These data indicate that the NO concentration of the inhaled gas in the order of magnitude of 1000 ppb has no impact on $N_{OPLAT}$. This is probably due to rapid uptake by hemoglobin in capillary blood.

Our data indicates that there was an almost thirty five-fold increase in mean $N_{OPLAT}$ as flow fell from 1550 to 4.2 ml/s. Rapid exhalations produced the lowest $N_{OPLAT}$ (range 2.0–5.7 ppb). The distribution of $N_{OPLAT}$ values was very narrow at high flow rates (3.2±1.4 ppb) and widened considerably at the 4.2 ml/s flow (110.6±54.8 ppb) with an almost eightfold variation between the lowest and highest values (FIG. 4A). This large variation in $N_{OPLAT}$ in this group of normal subjects is of unknown significance. When the same data were expressed as percentage change in $N_{OPLAT}$ related to the lowest flow (4.2 ml/s, FIG. 4B), the variation for all 10 subjects showed great uniformity of the effect of flow on $N_{OPLAT}$. It remains to be seen whether the nature of the NO/flow relationship varies among various disease groups. In contrast to $N_{OPLAT}$, mean NOe rose eleven-fold over the same flow range. This excretion rate is that present only during the steady expiratory flow. We are not aware of any other example in clinical measurement, where the measurement technique itself caused such a large change in the parameter being measured.

Other investigators have also observed a flow-dependence of exhaled NO concentration and excretion (13, 20), particularly in the context of exercise hyperventilation and resting hyperventilation. Iwamoto et al (12) reported that NO excretion rose on exercise and with voluntary hyperventilation at rest. Bauer et al (23) stated that exhaled NO and NO excretion rose in 4 subjects on exercise, and that exhaled NO concentration fell on resting hyperventilation. Massaro et al (22) however, reported no difference in NO concentration between a VC exhalation of 5 and 15 s. Our study expanded the examination of the NO-flow relationship by examining the flow spectrum from 1550 ml/s to 4.2 ml/s, so to determine the relevance of expiratory flow to clinical measurement technique in resting subjects. In addition, the relationship of $N_{OPLAT}$ to flow has been examined while confidently excluding nasal NO. Following our observation that changes in flow alone affect NO excretion, we do not believe that exhaled NO can reflect delivery of NO to the alveolus from the pulmonary vessels as has been proposed by some (12, 23). It is possible that the changes in ventilation alone during exercise could explain the changes in NO excretion observed on exercise (13, 20).

Although the application of a continuous expiratory pressure of 20 mm Hg may be anticipated to cause physiological effects such as decreased venous return or altered lung mechanics, the values obtained with the 60 mm Hg mouth pressure were not significantly different than those made with 20 mm Hg. It is likely that the lowest pressure which reliably closes the velum is acceptable for exhaled NO measurements as long as the flow is determined. Of interest is the apparent lack of effect on $N_{OPLAT}$ of the reduction in cardiac output which presumably occurred while maintaining the mouth pressure of 60 mm Hg. This again would support the contention that the NO measured is predominantly airway in origin and of a lesser degree that delivered to the alveolus through the vasculature, a view held by Persson et al (24) who examined the effects of PEEP on exhaled NO. The opposite view is proposed by Cremona et al (26, 27) who correlated exhaled NO with pulmonary vascular changes.

There are several important potential sources of error while using our technique. The major source of error is air leak either due to poor lip/mouthpiece seal, or from the nose or the apparatus. With any leak, the flow measured by the downstream pneumotachygraph will underestimate the actual flow through the airways, and the measured $N_{OPLAT}$ will decrease (FIG. 2). From examination of the steep gradient of the curves (FIG. 4A) at the lower flow rates, a small change in flow can have a large effect on $N_{OPLAT}$. Another source of error is lung volume, as shown by the TLC vs FRC study, where $N_{OPLAT}$ falls as lung volume decreases. The influence of lung volume on exhaled NO is possibly explained by decreased respiratory epithelial surface area affecting the amount of NO difflusing into the lumen. This concept was also proposed by Persson et al (24) to explain the increased NO due to PEEP. We have recently noted a fall in $N_{OPLAT}$ following bronchoconstriction with methacholine, which may also reflect the influence of lung volume on $N_{OPLAT}$. Lastly, no delay should occur from the inhalation to the exhalation, as NO accumulates in the airway continuously as shown by the breath hold experiment.

The interday variation (~20%) in $N_{OPLAT}$ indicates that any changes in $N_{OPLAT}$ due to disease or drug therapy must be interpreted in the context of spontaneous variation. The rho values however indicate that there is good interday and even better intraday reproducibility (Table 2). The intraday variation (~10%), which includes spontaneous measurement error, is small enough to suggest that NO$_{PLAT}$ can be measured without regard to the time of day during normal laboratory hours. Other physiological parameters, such as DLCO, also demonstrate similar intraday and interday variability.

We propose the following model to explain the marked variation in NO$_{PLAT}$ with expiratory flow (FIG. 6). Nitric oxide is produced mainly from the respiratory epithelium in keeping with the known presence of NO synthetases in this epithelium (25). As hemoglobin avidly takes up NO (28, 26, 29), alveolar air, in close equilibrium with capillary blood, has the lowest NO levels. As alveolar air enters and moves up the bronchial tree, there is transfer of NO from the bronchial wall to the lumen by gaseous diffusion. The NO diffusion rate depends on many factors including the NO concentration gradient between the wall and the lumen. This gradient is maximized by a large expiratory flow rate as the luminal NO concentration is kept low, and thus NO excretion rate rises with increase in flow. In contrast, the NO concentration falls with increasing flow as the contact time between air and bronchial wall falls. On theoretical grounds if the amount of NO transferred from bronchial wall to lumen was constant, (as would occur if the respiratory epithelium was impermeable to NO and the mechanism of transfer was active secretion alone), then NO concentration would still be flow-dependent, but NO excretion would be flow-independent. Exhaled NO, as assessed by NO$_{PLAT}$, is thus alveolar air which has been conditioned by passage through the bronchi.

An analogous relationship to that of NO$_{PLAT}$ with flow can be found in the physiology of respiratory heat loss (30, 21). As flow rises, respiratory heat loss (analogous to NOe) rises, while in contrast the temperature of the expired gas (analogous to NO concentration) falls. If this model is correct, then the bulk of the exhaled NO is derived from the airway epithelium, and thus predominantly reflects processes in the airways. In addition, this suggests that exhaled NO will be less reflective of NO produced in or delivered to the alveolus, and thus attempts to correlate NO levels with pulmonary vascular disease or lung ventilation/perfusion relationships may not be successful (23). We presume that alveolar NO concentration is best estimated using a rapid exhalation, as the air has less time to take up bronchial wall NO. However, in the ambulatory subject, this alveolar air can only be sampled after having traversed the conducting airways which themselves excrete NO. The NO present in alveolar air could be derived from inhaled environmental NO, from cells in the alveolar wall, or from NO delivered to the alveolus by pulmonary blood flow. It is not known whether alveolar NO values, as estimated by a rapid exhalation, will correlate with alveolar NO delivery, or merely reflect the equilibrium between NO in alveolar air and that bound to hemoglobin in capillary blood.

During breath hold, NO accumulated in the lumen until a steady state is reached between excretion and reabsorbtion. Breath hold NO values are of interest in showing the magnitude of the limits of NO accumulation in the airway, which are the same order of magnitude as the concentrations described in the nose but much less than that in the paranasal sinuses (9, 10, 14, 15). These measurements however are hard to perform and not suitable for clinical application, requiring over 60 s of breath hold.

Our technique reliably excludes nasal NO from the oral airflow and this is an essential feature of any exhaled NO measurement technique. Aside from this, the major implication of this study is that it is essential to measure NO concentrations at a constant standardized expiratory flow rate (whether by single breath or gas collection techniques). Vital capacity maneuvers at a constant flow rate are most practical and standardize lung volume, while tidal breathing, which is characterized by a continuous cyclical variation in expiratory flow, a short expiratory time, and breath to breath volume changes is not suitable. The use of high expiratory resistances, apart from causing velum closure, is essential to control low flow rates precisely. The dramatic almost eleven-fold change in mean NOe with increasing flow also has major implications for measurement techniques where exhaled gas is collected, as different flow rates and patterns will result in large variations in the amount of NO exhaled.

Figure 5B:
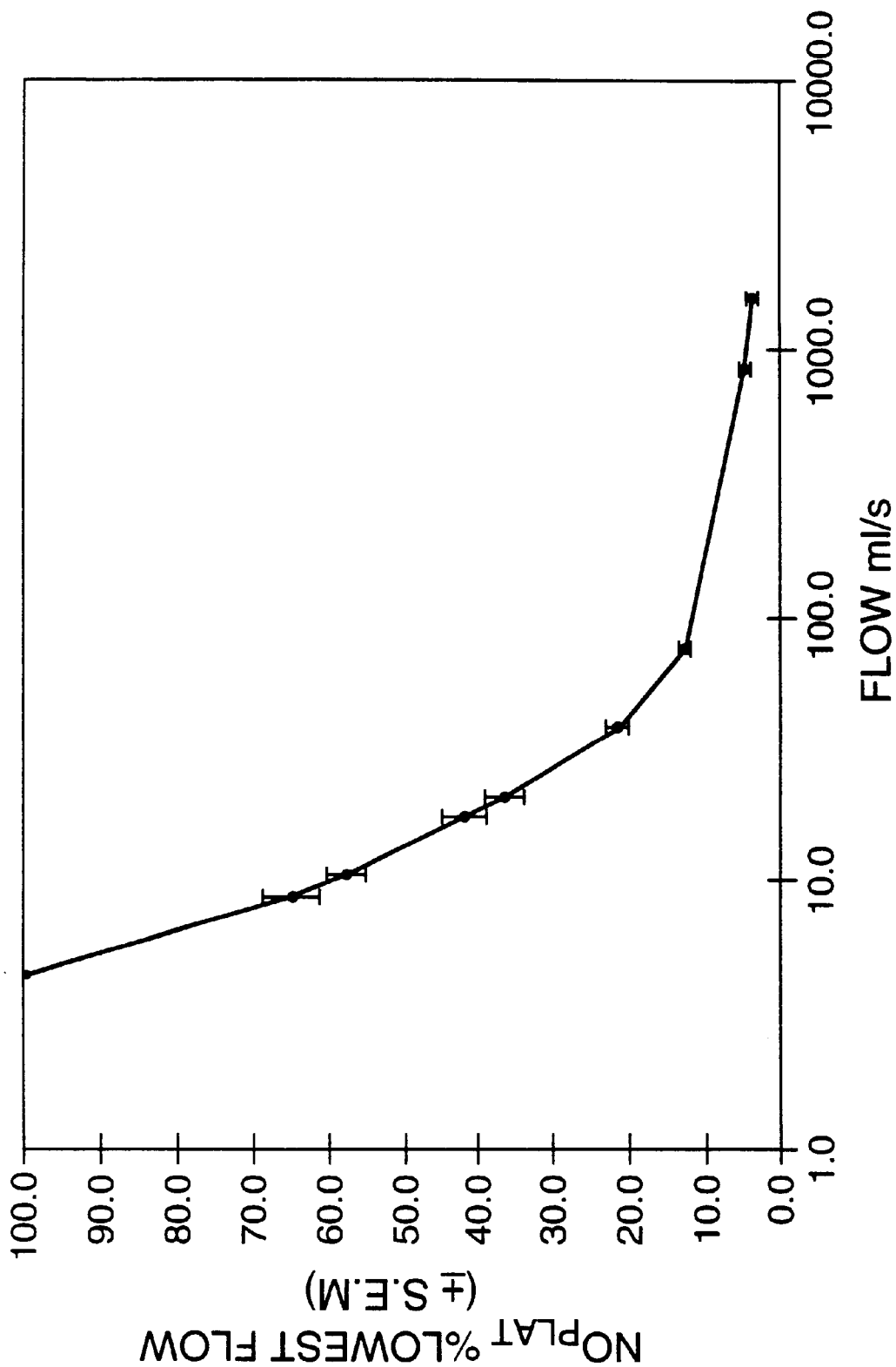
FIG. 5B shows the $NO_{PLAT}$ data expressed as percent of lowest flow value (4.2 ml/s) against log flow.

We believe that this high expiratory resistance, positive mouth pressure method is a reliable and reproducible technique suitable for use in patients. With flows in the range 1040 ml/s, the test time is 10–20 s which is acceptable to most patients. The measurement of expired NO at three low flow rates enables a three-point curve to be drawn and this may provide more information on the exhaled NO status of a subject, perhaps by analyzing the slope of the NO-flow curve in addition. However, the similar way in which NO$_{PLAT}$ (% of lowest flow) varied in all 10 subjects (FIG. 5B), suggests that measurement at one flow can predict the NO concentration at all flows and suffice, particularly if a patient is acutely ill, or in pediatric practice.

Measurement of NO at very low flow rates greatly amplifies the NO signal, and will probably allow a better distinction to be made between normal subjects and disease states. In addition, low flow rates avoid measurements near the analyzer detection limits. As we believe that the NO measured is mainly of airway origin, the technique is likely to be suitable for airway diseases but unlikely to aid in strictly parenchymal or pulmonary-vascular disease.

In accordance with previous authors (6, 7), in an on-going study using this technique, we have also observed that exhaled NO appears to be very high in asthmatic subjects as compared to normal subjects, and falls markedly after inhaled steroid therapy. Thus we believe that exhaled NO in asthma shows great promise as a useflil index of disease activity and the response to therapy.

Although the present invention has been described in detail with reference to the examples presented above, it is understood that various modifications can be made without departing from the spirit of the invention. For example, the NO plateau value at any flow expressed as a percentage of the NO plateau measured at the lowest flow appears to vary in a constant fashion with flow between subjects. When measured at any particular flow rate, NO plateau data could be normalized and a normalized NO plateau versus flow plot could be used to extrapolate back to a "standard flow rate." Accordingly, the invention is limited only by the following claims.

BIBLIOGRAPHY

1. Barnes, P. J. 1992. Neural mechanisms in asthma. [Review]. *British Medical Bulletin* 48: 149–168.
2. Barnes, P. J. and M. G. Belvisi. 1993. Nitric oxide and lung disease. [Review]. *Thorax* 48: 1034–1043.
3. Gaston, B., J. M. Drazen, J. Loscalzo, and J. S. Stamler. 1994. The biology of nitrogen oxides in the airways. [Review]. *American Journal of Respiratory & Critical Care Medicine* 149: 538–551.
4. Abman, S. H. 1994. Pathogenesis and treatment of neonatal and postnatal pulmonary hypertension. [Review]. *Current Opinion in Pediatrics* 6: 239–247.

5. Lammers, J. W., P. J. Barnes, and K. F. Chung. 1992. Nonadrenergic, noncholinergic airway inhibitory nerves. [Review]. *European Respiratory Journal* 5: 239–246.
6. Alving, K., E. Weitzberg, and J. M. Lundberg. 1993. Increased amount of nitric oxide in exhaled air of asthmatics. *European Respiratory Journal* 6: 1368–1370.
7. Kharitonov, S. A., D. Yates, R. A. Robbins, R. Logan-Sinclair, and E. A. Shinebourne. 1994. Increased nitric oxide in exhaled air of asthmatic patients. *Lancet* 343: 133–135.
8. Persson, M. G., O. Zetterstrom, V. Agrenius, E. Ihre, and L. E. Gustafsson. 1994. Single-breath nitric oxide measurements in asthmatic patients and smokers. *Lancet* 343: 146–147.
9. Lundberg, J. O., E. Weitzberg, S. L. Nordvall, R. Kuylenstierna, J. M. Lundberg, and K. Alving. 1994. Primarily nasal origin of exhaled nitric oxide and absence in Kartagener's syndrome. *European Respiratory Journal* 7: 1501–1504.
10. Schedin, U., C. Frostell, M. G. Persson, J. Jakobsson, G. Andersson, and L. E. Gustafsson. 1995. Contribution from upper and lower airways to exhaled endogenous nitric oxide in humans. *Acta Anaesthesiologica Scandinavica* 39: 327–332.
11. Rubinstein, I., P. A. McClean, R. Boucher, N. Zamel, J. J. Fredberg, and V. Hoffstein. 1995. Effect of mouthpiece, noseclips, and head position on airway area measured by acoustic reflections. *Journal of Applied Physiology* 63: 1469–1474.
12. Iwamoto, J., D. R. Pendergast, H. Suzuki, and J. A. Krasney. 1994. Effect of graded exercise on nitric oxide in expired air in humans. *Respiration Physiology* 97: 333–345.
13. Trolin, G., T. Anden, and G. Hedenstiema. Nitric oxide (NO) in expired air at rest and during exercise. *Acta Physiologica Scandinavica* 151: 159–163, 1994.
14. Gerlach, H., R. Rossaint, D. Pappert, M. Knorr, and K. J. Falke. 1994. Autoinhalation of nitric oxide after endogenous synthesis in nasopharynx [see comments]. *Lancet* 343: 518–519.
15. Lundberg, J. O., J. Rinder, E. Weitzberg, J. M. Lundberg, and K. Alving. 1994. Nasally exhaled nitric oxide in humans originates mainly in the paranasal sinuses. *Acta Physiologica Scandinavica* 152: 431–432.
16. Silkoff, P., Maurer, J., Keshanee, S., Kesten, S., MacClean, P., Slutsky, A. S., Zamel, N. A technique to minimise the contribution of nasal nitric oxide to that measured at the mouth in humans. 1994. *The American Journal Of Respiratory and Critical Care Medi* 151(4):A329 (Abstract).
17. Schilling, J., P. Holzer, M. Guggenbach, D. Gyurech, K. Marathia, and S. Geroulanos. Reduced endogenous nitric oxide in the exhaled air of smokers and hypertensives. *European Respiratory Journal* 7: 467–471, 1994.
18. Persson, M. G., B. Cederqvist, C. U. Wiklund, and L. E. Gustafsson. 1994. Ethanol causes decrements in airway excretion of endogenous nitric oxide in humans. *European Journal of Pharmacology* 270: 273–278.
19. Persson, M. G., T. Midtvedt, A. M. Leone, and L. E. Gustafsson. 1994. Ca(2+)-dependent and Ca(2+)-independent exhaled nitric oxide, presence in germ-free animals, and inhibition by arginine analogues. *European Journal of Pharmacology* 264: 13–20.
20. Persson, M. G., N. P. Wiklund, and L. E. Gustafsson. 1993. Endogenous nitric oxide in single exhalations and the change during exercise. *American Review of Respiratory Disease* 148: 1210–1214.
21. Ingenito, E. P., J. Solway, E. R. McFadden,Jr., B. M. Pichurko, E. G. Cravalho, and J. M. Drazen. 1986. Finite difference analysis of respiratory heat transfer. *Journal of Applied Physiology* 61: 2252–2259.
22. Massaro, A. F., B. Gaston, K. Dieter, C. Fanta, J. S. Stamler, and J. M. Drazen. 1995. Expired Nitric Oxide Levels during Treatrnent of Acute Asthma. *American Journal of Respiratory & Critical Care Medicine* 152: 800–803.
23. Bauer, J. A., J. A. Wald, S. Doran, and D. Soda. 1994. Endogenous nitric oxide in expired air: effects of acute exercise in humans. *Life Sciences* 55: 1903–1909.
24. Persson, M. G., P. A. Lonnqvist, and L. E. Gustafsson. 1995. Positive end-expiratory pressure ventilation elicits increases in endogenously formed nitric oxide as detected in air exhaled by rabbits. *Anesthesiology* 82: 969–974.
25. Hamid, Q., D. R. Sprin-gall, V. Riveros-Moreno, P. Chanez, P. Howarth, J. Bousquet, P. Godard, S. Holgate, and J. M. Polak. 1993. Induction of nitric oxide synthase in asthma. *Lancet* 342:1510–1513.
26. Cremona, G., T. Higenbottam, C. Borland, and B. Mist. 1994. Mixed expired nitric oxide in primary pulmonary hypertension in relation to lung diffision capacity. *QJM* 87: 547–551.
27. Cremona, G., T. Higenbottam, M. Takao, L. Hall, and E. A. Bower. 1995. Exhaled nitric oxide in isolated pig lungs. *Journal of Applied Physiology* 78: 59–63.
28. Borland, C. D. and Y. Cox. 1991. Effect of varying alveolar oxygen partial pressure on difflusing capacity for nitric oxide and carbon monoxide, membrane diff-using capacity and lung capillary blood volume. *Clinical Science* 81: 759–765.
29. Deliconstantinos, G., V. Villiotou, and J. C. Stavrides. 1994. Scavenging effects of hemoglobin and related heme containing compounds on nitric oxide, reactive oxidants and carcinogenic volatile nitrosocompounds of cigarette smoke. A new method for protection against the dangerous cigarette constituents. *Anticancer Research* 14: 2717–2726.
30. Burnet, H., M. Bascou-Bussac, C. Martin, and Y. Jammes. 1994. Relationship between Cr and breathing pattern in mechanically ventilated patients. *Journal of Applied Physiology* 77: 2703–2708.
31. Gustafsson, L. E., A. M. Leone, M. G. Persson, N. P. Wiklund, and S. Moncada 1991. Endogenous nitric oxide is present in the exhaled air of rabbits, guinea pigs and humans. *Biochemical & Biophysical Research Communications* 181: 852–857.
32. Kharitonov, S. A., G. Lubec, B. Lubec, M. Hjelm, and P. J. Barnes. 1995. L-arginine increases exhaled nitric oxide in normal human subjects. *Clinical Science* 88: 135–139.
33. Borland, C., Y. Cox, and T. Higenbottam. 1993. Measurement of exhaled nitric oxide in man. *Thorax* 48: 1160–1162.
34. Persson, M. G. et al., 1994. Single breath nitric oxide measurements in asthamatic patients and smokers. *The Lancet* 343:146–147.
35. Schedin, U. et al., 1995. Contribution from upper and lower airways to exhaled endogenous; nitric oxide in humans. *Acta anaesthesiologica Scandinavica* 39:327–332.
36. Kimberly, B. et al., 1996. Nasal contribution to exhaled nitric oxide at rest and during breathholding in humans. *Am J. Respir. Crit. Care Med.* 153:826–836.

TABLE 1

Published values and techniques for exhaled NO. Not all articles specify speed of exhalation or use of nose clip. [VC = vital capacity exhalation, TB = todal breathing, NC = nose clip, BH = breath hold, MGC = mixed gas concentration].

| Author | Exhalation Maneuver | NO (ppb) Non-asthamatic | Asthma untreated | Asthma inh. steroid |
|---|---|---|---|---|
| Gustafson (31) | VC (gas collected) | 8 ± 0.8 (MGC) | | |
| Kharitonov (7) | VC (30–45 s) | 80.2 ± 4.1 (peak) | 283 + 16 | 101 + 7 |
| Kharitonov (32) | VC (30–45 s) | 73.6 ± 9.63 (peak) | | |
| Persson (8) | slow VC (gas collected), NC 15s BH | 3.90 ± 4 (peak) | 62.6 ± 13.3 | |
| | VC (gas collection/end-expiratory concentration) | 7.2 ± 1.0 (NGC) | 12.6 ± 2.7 | |
| Persson (19) | TB, NC | 7.6 ± 0.7 | | |
| Persson (18) | VC (10–15 s), 5 s BH | 4.7 ± 1.2 (peak) | | |
| | VC (10–15 s), 30 s BH | 35 ± 14 (peak) | | |
| Schilling (17) | TB, NC, gas collection | 19 ± 8 male (MGC) 21 ± 7 female | | |
| Alving (6) | TB, NC | 9 ± 1 (plateua) | 24 ± 6 | |
| Borland (33) | VC (last litre gas collected) | 8.1 ± 3.3 | | |
| | TB, gas collection | 14.7 ± 3.8 | | |
| Lundberg (9) | VC | 7 ± 2 (plateau) | | |
| | oral breathing tracheostomy closed | 14 ± 2 (plateau) | | |
| | via tracheostomy | 2 ± 0 (plateau) | | |
| Iwamoto (12) | TB, NC, gas collection | 26.3 ± 19.0 (mean) | | |
| Bauer (23) | TB | 12.9 ± 2.4 (mean) | | |
| Massaro (22) | VC (5–15 s), NC | 6.2 ± 0.4 (mean) | 19.4 + 3.3 | 10.9 + 2.3 |

TABLE 2

Comparison of $NO_{PLAT}$ sampled at mouth with to that measured in upper trachea oropharynx and nasal cavity for an expiratory flow rate of 20.7 ml/s. Three exhalations performed at each site.

| | subject 1 $NO_{PLAT}$ (ppb) | subject 2 $NO_{PLAT}$ (ppb) |
|---|---|---|
| Intra-tracheal (at glottis) | 16.9 | 14.0 |
| Oropharynx | 16.7 | 14.1 |
| At mouth | 18.6 | 14.1 |
| Nasal Cavity NO (ppb) | 1105 | 814 |

TABLE 3

Results of interday and intraday variability in $NO_{PLAT}$ presented as coefficients of variation (CV) and the intraclass correlation (rho) for the three rates employed.

| n = 6 | intraday | | | interday | | |
|---|---|---|---|---|---|---|
| flow (ml/s) | CV (%) mean | CV (%) range | rho | CV (%) mean | rho | CV (%) range |
| 10.3 | 10.1 | 4.6–18.8 | .97 | 19.0 | .81 | 12.7–24.4 |
| 20.7 | 8.6 | 2.6–16.9 | .98 | 25.5 | .69 | 14.5–36.8 |
| 38.2 | 11.1 | 6.4–17.5 | .95 | 23.2 | .60 | 7.5–30.4 |

TABLE 4

Results of comparison $NO_{PLAT}$ (mean ± s.d., ppb) measured with exhalation from TLC to that measured from FRC, and $NO_{PLAT}$ measured with a mouth pressure of 20 m Hg to that measured with 60 m Hg.

| | volume (n = 10) | |
|---|---|---|
| FLOW (ml/s) | TLC | FRC |
| 10.3 | 89.0 ± 80.5 | 77.0 ± 79.3 |
| 20.7 | 55.5 ± 52.9 | 44.9 ± 40.2 |
| 38.2 | 35.5 ± 34.6 | 26.7 ± 22.6 |

| | pressure (n = 5) | |
|---|---|---|
| FLOW (ml/s) | 20 (mm Hg) | 60 (mm Hg) |
| 15 | 32.0 ± 8.5 | 25.9 ± 8.1 |
| 20 | 25.3 ± 6.9 | 22.9 ± 6.6 |
| 25 | 21.4 ± 5.7 | 19.7 ± 5.3 |
| 30 | 19.6 ± 6.1 | 17.0 ± 4.8 |
| 35 | 17.8 ± 6.3 | 14.9 ± 4.3 |

TABLE 5

$NO_{PLAT}$ (ppb) obtained after a 30 s breath hold, at an expiratory flow of 4.2 ml/s, and with a fast exhalation of 1550 ml/s.

| n = 10 | Breath hold (30 s) | Lowest flow (4.2 ml/s) | Highest flow (1550 ml/s) |
|---|---|---|---|
| $NO_{PLAT}$ (mean ± s.d.) | 176.2 ± 100.8 | 110.7 ± 54.8 | 3.2 ± 1.34 |

TABLE 5-continued $NO_{PLAT}$ (ppb) obtained after a 30 s breath hold, at an expiratory flow of 4.2 ml/s, and with a fast exhalation of 1550 ml/s.

| n = 10 | Breath hold (30 s) | Lowest flow (4.2 ml/s) | Highest flow (1550 ml/s) |
|---|---|---|---|
| $NO_{PLAT}$ (range) | 50.9–339 | 25.6—214 | 2.0–5.7 |

What is claimed is:

1. A method for measuring components of exhaled breath of a subject, comprising the steps of:
   causing the subject to exhale into an appropriate apparatus for receiving exhaled breath;
   increasing the pressure in the mouth of the subject to a level sufficient to cause the velum of the subject to close and isolate the nasopharynx during exhalation; and
   measuring the level of one or more components of the exhaled breath.

2. The method of claim 1, wherein said one or more components are selected from the group consisting of carbon dioxide, oxygen, nitric oxide, nitrogen, nitrogen dioxide, hydrogen peroxide, proteins, surfactants, DNA, acetone, ammonia, sulfur compounds, acetylene, carbon monoxide, ethane and pentane.

3. The method of claim 2, wherein said one or more components is nitric oxide.

4. The method of claim 1, further comprising the step of collecting one or more components of exhaled breath prior to said measuring step.

5. The method of claim 1, further comprising the step of monitoring nasal $CO_2$ to confirm velum closure.

6. The method of claim 1, wherein the measuring step further comprises the storing of exhaled breath for analysis at a later time.

7. The method of claim 6, wherein the exhaled breath is stored in a gas collection container.

8. The method of claim 7, wherein the gas collection container is a gas sampling bag.

9. The method of claim 1, wherein said one or more components substantially arises from the respiratory tract below the glottis.

10. The method of claim 9, wherein at least about 90% of said one or more components arises from the respiratory tract below the glottis.

11. The method of claim 9, further comprising the step of maintaining a constant flow rate of the exhaled breath of the subject.

12. The method of claim 11, wherein said constant flow rate is accomplished by a resistance means associated or in flow connection with said receiving apparatus.

13. The method of claim 12, wherein said one or more components is nitric oxide.

14. The method of claim 12, wherein said maintaining a constant flow rate is effected by providing the subject with an instantaneous display of the pressure of the exhaled breath and the subject adjusts the force of the exhalation to maintain a constant pressure.

15. An apparatus for measuring components of exhaled breath of a subject, comprising conduit means for receiving the exhaled breath from the subject; means for increasing the pressure in the mouth of the subject to a level sufficient to cause the velum of the subject to close and isolate the nasopharynx during exhalation; and means for measuring the level of one or more components of the received exhaled breath.

16. The apparatus of claim 15, further comprising means for monitoring nasal $CO_2$ to confirm velum closure.

17. The apparatus of claim 15, further comprising means for providing the subject with an instantaneous display of the pressure of the exhaled breath so that the subject can adjust the force of the exhalation to maintain a constant pressure.

18. The apparatus of claim 15, wherein said pressure increasing means is sufficient to substantially exclude the presence of components of exhaled breath arising from the respiratory tract above the velum.

19. The apparatus of claim 15, wherein said one or more components is selected from the group consisting of carbon dioxide, oxygen, nitric oxide, nitrogen, nitrogen dioxide, hydrogen peroxide, proteins, surfactants, DNA, acetone, ammonia, sulfur compounds, acetylene, carbon monoxide, ethane and pentane.

20. The apparatus of claim 19, wherein said one or more components is nitric oxide.

21. The apparatus of claim 15, further comprising means for the storing of exhaled breath for analysis at a later time.

22. The apparatus of claim 21, wherein the exhaled breath is stored in a gas collection container.

23. The apparatus of claim 22, wherein the gas collection container is a gas sampling bag.

* * * * *

US006010459C1

(12) EX PARTE REEXAMINATION CERTIFICATE (6209th)
United States Patent
Silkoff et al.

(10) Number: US 6,010,459 C1
(45) Certificate Issued: *Apr. 29, 2008

(54) METHOD AND APPARATUS FOR THE MEASUREMENT OF COMPONENTS OF EXHALED BREATH IN HUMANS

(75) Inventors: Philip E. Silkoff, Toronto (CA); Patricia A. McClean, Weston (CA)

(73) Assignee: Aperon Biosystems Corp., Palo Alto, CA (US)

Reexamination Request:
No. 90/008,309, Oct. 25, 2006

Reexamination Certificate for:
Patent No.: 6,010,459
Issued: Jan. 4, 2000
Appl. No.: 08/827,703
Filed: Apr. 9, 1997

(*) Notice: This patent is subject to a terminal disclaimer.

Related U.S. Application Data

(63) Continuation-in-part of application No. 08/629,594, filed on Apr. 9, 1996, now Pat. No. 5,795,787.
(60) Provisional application No. 60/017,251, filed on May 10, 1996.

(51) Int. Cl.
    *A61B 5/08* (2006.01)

(52) U.S. Cl. .................. 600/532; 600/529; 128/200.26
(58) Field of Classification Search .................. None
    See application file for complete search history.

(56) References Cited
    PUBLICATIONS

Logan Research Ltd., "LR2000 Series: A New Generation of Mobile Integrated, Clinical, Real–Time Nitric Oxide Gas Analysers," [Instructual Manual], 1996.

*Primary Examiner*—Beverly M. Flanagan

(57) ABSTRACT

Methods and related equipment for measuring components of exhaled breath of a subject are provided which involve causing the subject to exhale into an appropriate apparatus for receiving exhaled breath; increasing the pressure in the mouth of the subject to a level sufficient to close the vellum and isolate the nasopharynx during exhalation; a means of monitoring nasal $CO_2$ to conrirm vellum closure; and measuring the level of one or more components of the collected exhaled breath. Endogenous nitric oxide is a preferred component of exhaled breath for monitoring and analysis.

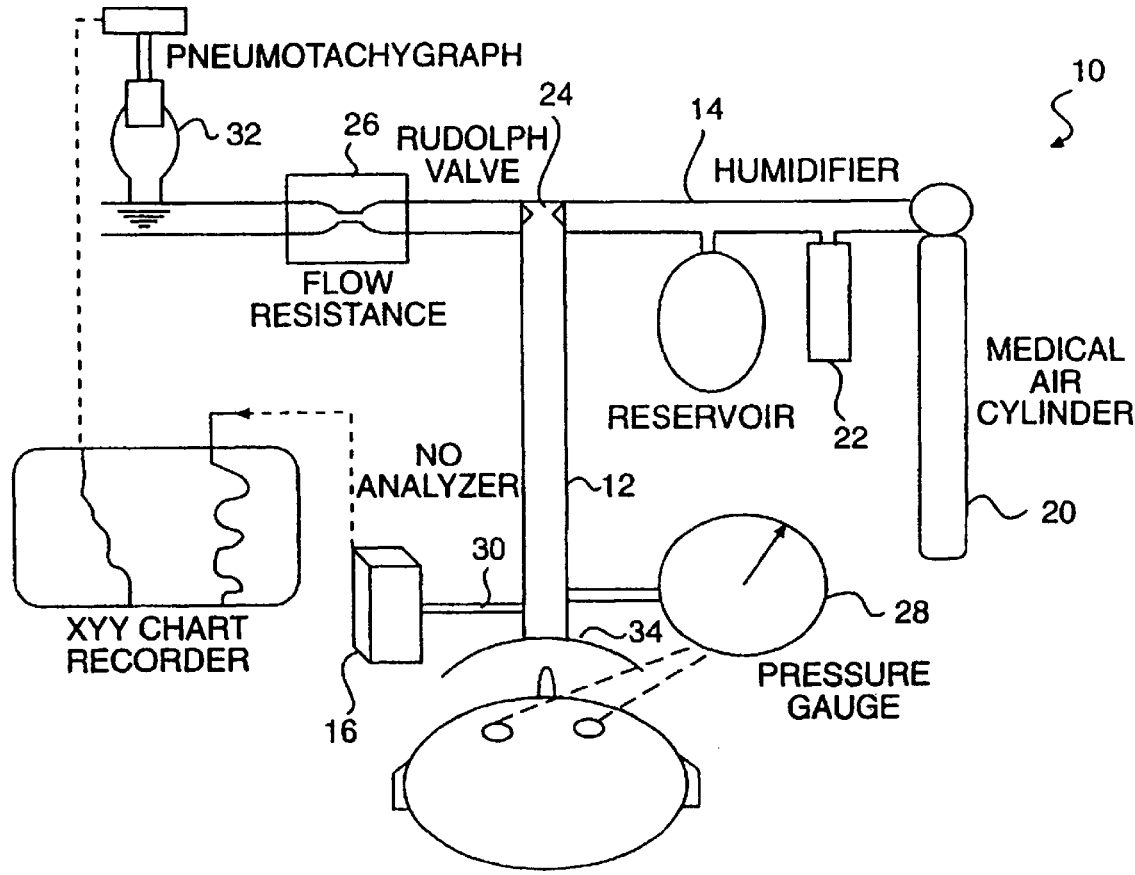

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 11, 13, 19 and 20 are cancelled.

Claims 1, 9, 10, 12, 14, 15 and 17 are determined to be patentable as amended.

Claims 4–8, 16, 18 and 21–23, dependent on an amended claim, are determined to be patentable.

New claims 24–26 are added and determined to be patentable.

1. A method for measuring components of exhaled breath of a subject, comprising the steps of:
   causing the subject to exhale into an appropriate apparatus for receiving exhaled breath *at a substantially constant low flow rate below 80 ml/sec*;
   increasing the pressure in the mouth of the subject to a level sufficient to cause the velum of the subject to close and isolate the nasopharynx during exhalation; and
   measuring the level of one or more components of the exhaled breath, *wherein the one or more components includes nitric oxide*.

9. The method of claim 1, wherein said [one or more components] *nitric oxide* substantially arises from the respiratory tract below the glottis.

10. The method of claim 9, wherein at least about 90% of said [one or more components] *nitric oxide* arises from the respiratory tract below the glottis.

12. The method of claim [11] *1*, wherein said constant flow rate is accomplished by a resistance means associated or in flow connection with said receiving apparatus.

14. The method of claim [12] *1*, wherein said maintaining a constant flow rate is effected by providing the subject with an instantaneous display of the pressure of the exhaled breath and the subject adjusts the force of the exhalation to maintain a constant pressure.

15. An apparatus for measuring components of exhaled breath of a subject, comprising*:*
   conduit means for receiving the exhaled breath from the subject;
   *means for causing the subject to exhale into the conduit means at a relatively low flow rate below 80 ml/sec;*
   means for increasing the pressure in the mouth of the subject to a level sufficient to cause the velum of the subject to close and isolate the nasopharynx during exhalation; and
   means for measuring the level of [one or more components] *nitric oxide* of the received exhaled breath.

17. The apparatus of claim 15, [further comprising] *wherein the constant flow exhalation means comprises* means for providing the subject with an instantaneous display of the pressure of the exhaled breath so that the subject can adjust the force of the exhalation to maintain a constant pressure.

*24. The apparatus of claim 15, wherein the constant flow exhalation means comprises means for providing the subject with an instantaneous indication of pressure for directing the subject to maintain a constant pressure.*

*25. The apparatus of claim 15, wherein the constant flow exhalation means comprises a flow resistance for maintaining said substantially constant flow rate.*

*26. The method of claim 1, wherein the pressure in the mouth is raised to a level sufficient to cause the velum of the subject to close and isolate the nasopharynx during exhalation in the absence of a nose clip.*

* * * * *